United States Patent
Arico et al.

(10) Patent No.: US 10,596,246 B2
(45) Date of Patent: Mar. 24, 2020

(54) ADJUVANTED COMBINATIONS OF MENINGOCOCCAL FACTOR H BINDING PROTEINS

(75) Inventors: Beatrice Maria Arico, Poggibonsi (IT); Brunella Brunelli, Grosseto (IT); Maurizio Comanducci, Castelnuovo Berardenga (IT); Mariagrazia Pizza, Siena (IT); Silvana Savino, Taverna Val di Pesa (IT); Maria Scarselli, Siena (IT)

(73) Assignee: GLAXOSMITHKLINE BIOLOGICAL SA, Rixensart (BE)

( * ) Notice: Subject to any disclaimer, the term of this patent is extended or adjusted under 35 U.S.C. 154(b) by 381 days.

(21) Appl. No.: 14/368,957

(22) PCT Filed: Dec. 29, 2011

(86) PCT No.: PCT/IB2011/056006
§ 371 (c)(1),
(2), (4) Date: Apr. 9, 2015

(87) PCT Pub. No.: WO2013/098589
PCT Pub. Date: Jul. 4, 2013

(65) Prior Publication Data
US 2015/0209419 A1    Jul. 30, 2015

(51) Int. Cl.
*A61K 39/095* (2006.01)
*A61K 47/64* (2017.01)
*A61K 39/09* (2006.01)
*A61K 39/00* (2006.01)
*A61K 39/39* (2006.01)

(52) U.S. Cl.
CPC .......... *A61K 39/095* (2013.01); *A61K 39/092* (2013.01); *A61K 39/39* (2013.01); *A61K 47/646* (2017.08); *A61K 2039/55505* (2013.01)

(58) Field of Classification Search
None
See application file for complete search history.

(56) References Cited

U.S. PATENT DOCUMENTS

| | | |
|---|---|---|
| 4,057,685 A | 11/1977 | McIntire |
| 4,459,286 A | 7/1984 | Hilleman et al. |
| 4,663,160 A | 5/1987 | Tsay et al. |
| 4,673,574 A | 6/1987 | Anderson |
| 4,761,283 A | 8/1988 | Anderson |
| 4,808,700 A | 2/1989 | Anderson et al. |
| 4,965,338 A | 10/1990 | Tabankia et al. |
| 5,204,098 A | 4/1993 | Szu et al. |
| 5,425,946 A | 6/1995 | Tai et al. |
| 5,698,438 A | 12/1997 | Stojiljkovic et al. |
| 6,531,131 B1 | 3/2003 | Gu et al. |
| 6,645,503 B1 | 11/2003 | Arumugham et al. |
| 7,785,608 B2 * | 8/2010 | Zlotnick ................ C07K 14/22 424/130.1 |
| 8,563,006 B2 * | 10/2013 | Zlotnick ................ C07K 14/22 424/184.1 |
| 2006/0228380 A1 | 10/2006 | Hausdorff et al. |
| 2006/0228381 A1 | 10/2006 | Bahler et al. |
| 2006/0251670 A1 * | 11/2006 | Comanducci ........ A61K 39/095 424/190.1 |
| 2007/0184071 A1 | 8/2007 | Hausdorff et al. |
| 2007/0184072 A1 | 8/2007 | Hausdorff et al. |
| 2007/0231340 A1 | 10/2007 | Hausdorff et al. |
| 2008/0102498 A1 | 5/2008 | Bahler et al. |
| 2013/0189295 A1 | 7/2013 | Arico et al. |

FOREIGN PATENT DOCUMENTS

| | | |
|---|---|---|
| EP | 0208375 A2 | 1/1987 |
| EP | 0378881 A1 | 7/1990 |
| EP | 0427347 A1 | 5/1991 |
| EP | 0471177 A2 | 2/1992 |
| EP | 0594610 A1 | 5/1994 |
| WO | 199101146 A1 | 2/1991 |
| WO | 199317712 A2 | 9/1993 |
| WO | 199403208 A1 | 2/1994 |
| WO | 199405325 A1 | 3/1994 |
| WO | 199408021 A1 | 4/1994 |
| WO | 199629412 A1 | 9/1996 |
| WO | 199853851 A1 | 12/1998 |
| WO | 199858668 A2 | 12/1998 |
| WO | 199957280 A2 | 11/1999 |
| WO | 200010599 A2 | 3/2000 |
| WO | 200023595 A1 | 4/2000 |
| WO | 200026384 A1 | 5/2000 |
| WO | 200033882 A1 | 6/2000 |
| WO | 200056360 A2 | 9/2000 |

(Continued)

OTHER PUBLICATIONS

Greenspan et al. Nature Biotechnology 17:936-937, 1999.*
Skolnick et al. Trends in Biotechnology 18: 34-39, 2000.*
Lazar et al. Mol. Cellular Biol. 8: 1247-1252, 1988.*
Rudinger J. In: Peptide Hormones. (Ed) JA Parsons, University Park Press, pp. 1-7, 1976.*
Jones et al., Effects of Adsorption to Aluminum Salt Adjuvants on the Structure and Stability of Model Protein Antigens, 2005 Journal of Biological Chemistry 280(14): 13406-13414.
European Patent Office as International Search Authority, Written Opinion and International Search Report for International Application No. PCT/IB2011/056006 dated Nov. 13, 2012; 19 total pages.
European Patent Office as International Preliminary Examining Authority, International Preliminary Report on Patentability for International Application No. PCT/IB2011/056006 dated Mar. 26, 2014; 23 total pages.

(Continued)

Primary Examiner — Sarvamangala Devi

(57) ABSTRACT

The M01573 sequence of meningococcal fHbp offers poor coverage in a vaccine. The invention addresses this poor coverage in two ways. In a first aspect, a fHbp-based vaccine includes two family I fHbp sequences, one which is more closely related to MC58 than to M01573, and vice versa. In a second aspect, a multi-family fHbp-based vaccine uses a family I fHbp sequence which is more closely related to MC58 than to M01573, in combination with a family III fHbp sequence. The compositions are adjuvanted with an aluminium phosphate adjuvant.

4 Claims, 2 Drawing Sheets

Specification includes a Sequence Listing.

(56) References Cited

FOREIGN PATENT DOCUMENTS

| | | | |
|---|---|---|---|
| WO | 200061761 A2 | 10/2000 | |
| WO | 200066741 A2 | 11/2000 | |
| WO | 200122992 A2 | 4/2001 | |
| WO | 200138350 A2 | 5/2001 | |
| WO | 200155182 A1 | 8/2001 | |
| WO | 200172337 A1 | 10/2001 | |
| WO | 2002091998 A2 | 11/2002 | |
| WO | 2003020756 A2 | 3/2003 | |
| WO | 2003063766 A2 | 8/2003 | |
| WO | 2003070282 A2 | 8/2003 | |
| WO | 2003080678 A1 | 10/2003 | |
| WO | 2004014417 A2 | 2/2004 | |
| WO | 2004015099 A2 | 2/2004 | |
| WO | 2004048404 A2 | 6/2004 | |
| WO | 2004094596 A2 | 11/2004 | |
| WO | 2005033148 A1 | 4/2005 | |
| WO | 2006024954 A2 | 3/2006 | |
| WO | 2007000314 A2 | 1/2007 | |
| WO | 2007000341 A2 | 1/2007 | |
| WO | 2007000342 A2 | 1/2007 | |
| WO | 2007000343 A2 | 1/2007 | |
| WO | 2007060548 A2 | 5/2007 | |
| WO | 2007071707 A2 | 6/2007 | |
| WO | 2007127665 A2 | 11/2007 | |
| WO | 2007144316 A2 | 12/2007 | |
| WO | 2007144317 A2 | 12/2007 | |
| WO | 2008079372 A2 | 7/2008 | |
| WO | 2008143709 A2 | 11/2008 | |
| WO | 2009038889 A1 | 3/2009 | |
| WO | 2009104097 A2 | 8/2009 | |
| WO | 2010109323 A1 | 9/2010 | |
| WO | 2011161653 A1 | 12/2011 | |
| WO | 2012025873 A2 | 3/2012 | |
| WO | 2012032489 A1 | 3/2012 | |

OTHER PUBLICATIONS

Wang and Frasch, Development of a Neisseria meningitides Group B Serotype 2b Protein Vaccine and Evaluation in a Mouse Model, 1984 Infection and Immunity 46(2): 408-414.

Koeberling et al., Meningococcal outer membrane vesicle vaccines derived from mutant strains engineered to express factor H binding proteins from antigenic variant groups 1 and 2, 2009 Clin. Vaccine Immunol. 16(2): 156-162.

Jiang et al., Broad vaccine coverage predicted for a bivalent recombinant factor H binding protein based vaccine to prevent serogroup B meningococcal disease, 2010 Vaccine 28: 6086-6093.

Anderson et al., Poster Abstract No. P100 on pp. 170 to 171 entitled "Functional cross-reactive antibodies are elicited by a Group B Neisseria meningitidis bivalent recombinant lipidated LP2086 vaccine in Cynomolgus macaques" for the 16th International Pathogenic Neisseria Conference Jul. 7, 2008 in Rotterdam, The Netherlands, available at http://neisseria.org/ipnc/2008/Abstracts_poster_presentations_IPNC_2008.pdf (last visited Feb. 22, 2017).

Masignani et al., Vaccination against Neisseria meningitidis using three variants of the lipoprotein GNA1870, 2003 J. Exper. Med. 197(6): 789-799.

Fletcher et al., Vaccine potential of the Neisseria meningitidis 2086 lipoprotein, 2004 Infect. Immun. &2(4): 2088-2100.

Panatto et al., Neisseria meningitidis B vaccines, 2011 Expert Rev. Vaccines 10(9): 1337-1351.

Granoff, D.M., Review of meningococcal group B vaccines, 2010 Clin. Infect. Dis. 50(S4): S54 ; 23 total pages.

Brunelli et al., Influence of sequence variability on bactericidal activity sera induced by Factor H binding protein variant 1.1., 2011 Vaccine 3(91) : 1072-1081.

Scarselli et al., Rational design of a meningococcal antigen inducing broad protective immunity, 2011 Sci. Transl. Med. 3(91): 91ra62; 12 total pages.

Richmond et al., Poster Abstract No. P212 on pp. 270 to 271 entitled "A randomized, observer-blinded, active control, phase 1 trial of meningococcal serogroup B rLP2086 vaccine in healthy children and adolescents aged 8 to 14 years" for the 16th International Pathogenic Neisseria Conference Jul. 7, 2008 in Rotterdam, The Netherlands, available at http://neisseria.org/ipnc/2008/Abstracts_poster_presentations_IPNC_2008.pdf (last visited Feb. 22, 2017).

Marshall et al., Poster Abstract No. P213 on pp. 271 to 272 entitled "A randomized, placebo-controlled, double-blind, phase 1 trial of ascending doses of meningococcal group B rLP2086 vaccine in healthy adults" for the 16th International Pathogenic Neisseria Conference Jul. 7, 2008 in Rotterdam, The Netherlands, available at http://neisseria.org/ipnc/2008/Abstracts_poster_presentations_IPNC_2008.pdf (last visited Feb. 22, 2017).

Arakere et al., Specificity of antibodies to O-acetyl-positive and O-acetyl-negative group C meningococcal polysaccharides in sera from vaccinees and carriers. Infect Immun. Dec. 1991;59(12):4349-56.

Baraldo et al., N19 polyepitope as a carver for enhanced immunogenicity and protective efficacy of meningococcal conjugate vaccines. Infect Immun. Aug. 2004;72(8):4884-7.

Beernink et al., Rapid genetic grouping of factor h-binding protein (genome-derived neisserial antigen 1870), a promising group B meningococcal vaccine candidate. Clin Vaccine Immunol. Jul. 2006;13(7):758-63.

Bethell et al., A novel method of activation of cross-linked agaroses with 1,1'-carbonyldiimidazole which gives a matrix for affinity chromatography devoid of additional charged groups. J Biol Chem. Apr. 25, 1979;254(8):2572-4.

Brusic et al., Prediction of MHC class II-binding peptides using an evolutionary algorithm and artificial neural network. Bioinformatics. 1998;14(2):121-30.

Bublil et al., Stepwise prediction of conformational discontinuous B-cell epitopes using the Mapitope algorithm. Proteins. Jul. 1, 2007;68(1):294-304.

Burrell et al., Aluminium phosphate adjuvants prepared by precipitation at constant pH. Part I: composition and structure. Vaccine. Sep. 15, 2000;19(2-3):275-81.

Cantini et al., Solution structure of the immunodominant domain of protective antigen GNA1870 of Neisseria meningitidis. J Biol Chem. Mar. 17, 2006;281(11):7220-7.

Carter, J.M., Epitope mapping of a protein using the Geysen (PEPSCAN) procedure, Chapter 12 on pp. 207-223 in Methods Mol. Biol. vol. 36 1994 (eds. Dunn and Pennington, Humana Press Inc., Totowa NJ).

Chen et al., Prediction of linear B-cell epitopes using amino acid pair antigenicity scale. Amino Acids. Sep. 2007;33(3):423-8.

Comanducci et al., NadA, a novel vaccine candidate of Neisseria meningitidis. J Exp Med. Jun. 3, 2002;195(11):1445-54.

Davenport et al., An empirical method for the prediction of T-cell epitopes. Immunogenetics. 1995;42(5):392-7.

De Lalla et al., Cutting edge: identification of novel T cell epitopes in Lol p5a by computational prediction. J Immunol. Aug. 15, 1999;163(4):1725-9.

Dunning Hotopp et al., Comparative genomics of Neisseria meningitidis: core genome, islands of horizontal transfer and pathogen-specific genes. Microbiology. Dec. 2006;152(Pt 12)3733-49.

Falugi et al., Rationally designed strings of promiscuous CD4(+) T cell epitopes provide help to Haemophilus influenzae type b oligosaccharide: a model for new conjugate vaccines. Eur J Immunol. Dec. 2001;31(12):3816-24.

Feller et al., Identifying antigenic T-cell sites. Nature. Feb. 21, 1991;349(6311):720-1.

Frasch et al., Bactericidal antibody is the immunologic surrogate of protection against meningococcal disease. Vaccine. Jun. 24, 2009;27 Suppl 2:B112-6.

Geyer et al., Immunochemical properties of oligosaccharide-protein conjugates with Klebsiella-K2 specificity. I. Specificity and crossreactivity of anti-conjugate versus anti-bacterial antibodies. Med Microbiol Immunol. Jan. 24, 1979;165(4):271-88.

Geysen et al., Use of peptide synthesis to probe viral antigens for epitopes to a resolution of a single amino acid. Proc Natl Acad Sci U S A. Jul. 1984;81(13):3998-4002.

(56) References Cited

OTHER PUBLICATIONS

Giuliani et al., A universal vaccine for serogroup B meningococcus. Proc Natl Acad Sci U S A. Jul. 18, 2006;103(29):10834-9.

Giuliani et al., The region comprising amino acids 100 to 255 of Neisseria meningitidis lipoprotein GNA 1870 elicits bactericidal antibodies. Infect Immun. Feb. 2005;73(2):1151-60.

Glode et al., Comparative immunogenicity of vaccines prepared from capsular polysaccharides of group C Neisseria meningitidis O-acetyl-positive and O-acetyl-negative variants and *Escherichia coli* K92 in adult volunteers. J Infect Dis. Jan. 1979;139(1):52-9.

Goldschneider et al., Human immunity to the meningococcus. I. The role of humoral antibodies. J Exp Med. Jun. 1, 1969;129(6):1307-26.

Hearn et al., Application of 1,1'-carbonyldiimidazole-activated matrices for the purification of proteins. III. The use of 1,1'-carbonyldiimidazole-activated agaroses in the biospecific affinity chromatographic isolation of serum antibodies. J Chromatogr. Nov. 20, 1981;218:509-18.

Hou et al., Protective antibody responses elicited by a meningococcal outer membrane vesicle vaccine with overexpressed genome-derived neisserial antigen 1870. J Infect Dis. Aug. 15, 2005;192(4):580-90.

Jameson et al., The antigenic index: a novel algorithm for predicting antigenic determinants. Comput Appl Biosci. Mar. 1988;4(1):181-6.

Jodar et al., Serological criteria for evaluation and licensure of new pneumococcal conjugate vaccine formulations for use in infants. Vaccine. Jul. 4, 2003;21(23):3265-72.

Kuo et al., Characterization of a recombinant pneumolysin and its use as a protein carrier for pneumococcal type 18C conjugate vaccines. Infect Immun. Jul. 1995;63(7):2706-13.

Kwok et al., Rapid epitope identification from complex class-II-restricted T-cell antigens. Trends Immunol. Nov. 2001;22(11):583-8.

Maksyutov et al., ADEPT: a computer program for prediction of protein antigenic determinants. Comput Appl Biosci. Jun. 1993;9(3):291-7.

Martin et al., Highly conserved Neisseria meningitidis surface protein confers protection against experimental Infection. J Exp Med. Apr. 7, 1997;185(7):1173-83.

Mascioni et al., Structural Basis for the Immunogenic Properties of the Meningococcal Vaccine Candidate LP2086. J Biol Chem. Mar. 27, 2009;284(13):8738-46.

Meister et al., Two novel T cell epitope prediction algorithms based on MHC-binding motifs; comparison of predicted and published epitopes from *Mycobacterium tuberculosis* and HIV protein sequences. Vaccine. Apr. 1995;13(6):581-91.

Metruccio et al., A novel phase variation mechanism in the meningococcus driven by a ligand-responsive repressor and differential spacing of distal promoter elements. PLoS Pathog. Dec. 2009;5(12):e1000710.

Michon et al., Structure activity studies on group C meningococcal polysaccharide-protein conjugate vaccines: effect of O-acetylation on the nature of the protective epitope. Dev Biol (Basel). 2000;103:151-60.

Michon et al., Multivalent pneumococcal capsular polysaccharide conjugate vaccines employing genetically detoxified pneumolysin as a carrier protein. Vaccine. Nov. 1998;16(18):1732-41.

Oriente et al., Expression of factor H binding protein of meningococcus responds to oxygen limitation through a dedicated FNR-regulated promoter. J Bacteriol. Feb. 2010;192(3):691-701.

Pajon et al., Frequency of factor H-binding protein modular groups and susceptibility to cross-reactive bactericidal activity in invasive meningococcal isolates. Vaccine. Feb. 25, 2010;28(9):2122-9.

Perkins-Balding et al., Identification of functionally important regions of a haemoglobin receptor from Neisseria meningitidis. Microbiology. Dec. 2003;149(Pt 12):3423-35.

Porro et al., Specific antibodies to diphtheria toxin and type 6A pneumococcal capsular polysaccharide induced by a model of semi-synthetic glycoconjugate antigen. Mol Immunol. Aug. 1985;22(8):907-19.

Raddrizzani et al., Epitope scanning using virtual matrix-based algorithms. Brief Bioinform. May 2000;1(2):179-89.

Ram et al., Neisserial lipooligosaccharide is a target for complement component C4b. Inner core phosphoethanolamine residues define C4b linkage specificity. J Biol Chem. Dec. 19, 2003;278(51):50853-62.

Roberts et al., Prediction of HIV peptide epitopes by a novel algorithm. AIDS Res Hum Retroviruses. May 1, 1996;12(7):593-610.

Ruan et al., Protein D of Haemophilus influenzae. A novel bacterial surface protein with affinity for human IgD. J Immunol. Nov. 15, 1990;145(10):3379-84.

Rubinstein et al., Murine immune response to the Neisseria meningitidis group C capsular polysaccharide. II. Specificity. J Immunol. Dec. 15, 1988;141(12):4357-62.

Santos et al., Importance of complement source in measuring meningococcal bactericidal titers. Clin Diagn Lab Immunol. May 2001;8(3):616-23.

Schirle et al., Combining computer algorithms with experimental approaches permits the rapid and accurate identification of T cell epitopes from defined antigens. J Immunol Methods. Nov. 1, 2001;257(1-2):1-16.

Tettelin et al., Complete genome sequence of Neisseria meningitidis serogroup B strain MC58. Science. Mar. 10, 2000;287(5459):1809-15.

Tong et al., Methods and protocols for prediction of immunogenic epitopes. Brief Bioinform. Mar. 2007;8(2):96-108.

Tsurui et al., Prediction of T-cell epitope. J Pharmacol Sci. Dec. 2007;105(4):299-316.

Welling et al., Prediction of sequential antigenic regions in proteins. FEBS Lett. Sep. 2, 1985;188(2):215-8.

Welsch et al., Protective activity of monoclonal antibodies to genome-derived neisserial antigen 1870, a Neisseria meningitidis candidate vaccine. J Immunol. May 1, 2004;172(9):5606-15.

World Health Organization, WHO Expert Committee on Biological Standardization Fifty-fourth report, Annex 2 in the WHO Technical Report Series No. 927 at pp. 64-98, Geneva 2005, 35 total pages.

Zhu et al., Evaluation of recombinant lipidated P2086 protein as a vaccine candidate for group B Neisseria meningitidis in a murine nasal challenge model. Infect Immun. Oct. 2005;73(10):6838-45.

Seid et al., Characterization of Diverse Subvariants of the Meningococcal Factor H (fH) Binding Protein for Their Ability to Bind fH, To Mediate Serum Resistance, and to Induce Bactericidal Antibodies, 2011 Inf. & Immun. 79(2):970-981.

Raghava and Barton, Quantification of the variation in percentage identity for protein sequence alignments, 2006 BMC Bioinformatics 7:415, 4 pages.

* cited by examiner

ADJUVANTED COMBINATIONS OF MENINGOCOCCAL FACTOR H BINDING PROTEINS

CROSS REFERENCE TO RELATED APPLICATIONS

This application is the U.S. National Stage of International Application No. PCT/IB2011/056006, filed Dec. 29, 2011 and published in English, which is incorporated by reference in its entirety.

SEQUENCE LISTING

The instant application contains a Sequence Listing which has been submitted electronically in connection with International Application No. PCT/IB2011/056006 in ASCII format, and is hereby incorporated by reference in its entirety. Said ASCII copy, created on Dec. 23, 2011, is named PAT054956-WO-PCT Seqlist ST25.txt and is 82,723 bytes in size.

TECHNICAL FIELD

The invention is in the field of meningococcal vaccines, in particular those containing fHbp.

BACKGROUND ART

*Neisseria meningitidis* (meningococcus) is a Gram-negative spherical bacterium. Current meningococcal vaccines are also based on capsular saccharides. These include monovalent serogroup C conjugate vaccines and 4-valent conjugate mixtures for serogroups A, C, W135 and Y. There is currently no useful vaccine authorised for general use against serogroup B ('MenB').

One antigen which has been proposed for use in immunising against MenB is the factor H binding protein ('fHbp'). This antigen has also been called protein '741' (SEQ IDs 2535 & 2536 in ref 34), 'NMB1870', 'GNA1870' [refs. 1-3], 'P2086', 'LP2086' or 'ORF2086' [4-6]. The protein has been well studied. It is naturally a lipoprotein and is expressed across all meningococcal serogroups. The structure of fHbp's C-terminal immunodominant domain ('fHbpC') has been determined by NMR [7]. This part of the protein forms an eight-stranded β-barrel, whose strands are connected by loops of variable lengths. The barrel is preceded by a short α-helix and by a flexible N-terminal tail.

The fHbp antigen falls into three distinct variants or families [8] and it has been found that serum raised against a given family is bactericidal within the same family, but is not active against strains which express one of the other two families i.e. there is intra-family cross-protection, but not inter-family cross-protection. Thus reference 8 proposes to combine different variants of fHbp into a single vaccine composition, thereby increasing strain coverage, either as a mixture of separate proteins or as a fusion protein of the different variants (the latter being 'tandem proteins').

DISCLOSURE OF THE INVENTION

Family I of fHbp includes strain MC58, which is the strain which was used for the first genomic sequence publication [9] and is available from the ATCC as "BAA-335". The MC58 sequence for fHbp is SEQ ID NO: 1 herein, shown in SEQ ID NO: 26 starting at the cysteine at the N-terminus of the mature meningococcal protein. Family I also includes strain M01573 [5], whose sequence is SEQ ID NO: 23 herein (also referred to as the "B01" or "CDC1573" sequence; see database entry GI:40353481). SEQ ID NOs: 23 and 26 are aligned below.

Although the M01573 fHbp sequence is proposed for use in a human vaccine [10], and despite its close sequence relationship to fHbp from strain MC58, the inventors have found that serum raised against the M01573 sequence offers poor protection against the MC58 strain. As MC58 is representative of at least 30% of circulating family I strains, the M01573 sequence thus offers poor coverage of family I. It is an object of the invention to address this poor coverage, and to provide further and improved vaccine compositions which include fHbp antigens from multiple families. In broad terms, this object is achieved in two ways:

In a first aspect, a fHbp-based vaccine includes two family I fHbp sequences, one which is more closely related to MC58 (SEQ ID NO: 1) than to M01573 (SEQ ID NO: 23), and the other vice versa. Thus the invention provides an immunogenic composition which comprises a first fHbp antigen and a second fHbp antigen, wherein: the first fHbp antigen comprises an amino acid sequence which is more closely related to SEQ ID NO: 1 than to SEQ ID NO: 23; and the second fHbp antigen comprises an amino acid sequence which is more closely related to SEQ ID NO: 23 than to SEQ ID NO: 1. As explained in more detail below, this immunogenic composition can include further antigen components in addition to these two fHbp antigens.

In a second aspect, a multi-family fHbp-based vaccine uses a family I sequence which is more closely related to MC58 than to M01573, in combination with a family III sequence (e.g. SEQ ID NO: 25 from strain M01240320). Thus the invention provides an immunogenic composition which comprises a first fHbp antigen and a second fHbp antigen, wherein: the first fHbp antigen comprises an amino acid sequence which is more closely related to SEQ ID NO: 1 than to SEQ ID NO: 23; and the second fHbp antigen comprises an amino acid sequence (i) having at least w % sequence identity to SEQ ID NO: 25 and/or (ii) consisting of a fragment of at least x contiguous amino acids from SEQ ID NO: 25. The value of w is at least 94 (e.g. 95, 96, 97, 98, 99 or more). The value of x is either (a) at least 50 e.g. 55, 60, 65, 70, 75, 80, 85, 90, 95, 100, 110, 120, 130, 140, 150, 160, 180, 200 or (b) at least 7 (e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200), provided that the fragment is not also a fragment of SEQ ID NO: 2 and/or of SEQ ID NO: 3. The first and second fHbp antigens have different amino acid sequences. As explained in more detail below, this immunogenic composition can include further antigen components in addition to these two fHbp antigens but, preferably, it does not include a fHbp antigen comprising an amino acid sequence with ≥95% identity to SEQ ID NO: 23.

Immunogenic compositions of the invention are adjuvanted. The adjuvant comprises an aluminium phosphate salt (see below).

Factor H Binding Protein(s) Compositions of the invention include at least two different meningococcal factor H binding proteins (fHbp) to generate distinct immune responses which are not fully cross-reactive and which provide a broader spectrum of strain coverage against meningococci that the single fHbps alone.

In the invention's first aspect, a composition includes two family I fHbp antigen sequences. The first of these is more closely related to MC58 than to M01573; the second is more closely related to M01573 than to MC58. In the invention's aspect, a composition includes a fHbp which is more closely related to MC58 than to M01573. A fHbp antigen sequence may be defined as more closely related to MC58 than to M01573 if it meets one or more of the following criteria:

(a) it can elicit antibodies in a mouse which recognise a wild-type meningococcal fHbp comprising SEQ ID NO: 1 but which, under the same binding conditions, do not recognise a wild-type meningococcal fHbp comprising SEQ ID NO: 4 [NB: it may elicit some antibodies which recognise both SEQ ID NOs: 1 and 4].

(b) it can elicit antibodies in a mouse which are bactericidal against strain MC58 in a serum bactericidal assay; for example, providing a serum bactericidal titer of ≥1:4 using the Goldschneider assay with human complement [11-13], and/or providing a serum bactericidal titer of ≥1:128 using baby rabbit complement.

(c) it has at least 75% sequence identity to both of SEQ ID NO: 1 and SEQ ID NO: 23, but it has a higher sequence identity to SEQ ID NO: 1 than to SEQ ID NO: 23, when aligned using the same algorithm and parameters.

(d) it includes one or more of the 6-mers listed as SEQ ID NOs: 27 to 37. NB: the 6-mers of SEQ ID NOs: 27 to 34 may overlap in the sequence, and the 6-mers of SEQ ID NOs: 36 & 37 may overlap in the sequence.

(e) when aligned with SEQ ID NO: 1, it does not have a threonine residue (and preferably has an alanine residue) at the amino acid residue which aligns with Ala-2 of SEQ ID NO:1.

(f) when aligned with SEQ ID NO: 1, it does not have a valine residue (and preferably has a glycine residue) at the amino acid residue which aligns with Gly-141 of SEQ ID NO:1.

Of these six criteria, a sequence preferably meets at least criterion (b) or (c), more preferably at least (b) & (c), even more preferably at least (a), (b) & (c), and most preferably all six.

For the first aspect, a fHbp antigen sequence may be defined as more closely related to M01573 than to MC58 if it meets one or more of the following criteria:

(a) it can elicit antibodies in a mouse which recognise a wild-type meningococcal fHbp comprising SEQ ID NO: 4 but which, under the same binding conditions, do not recognise a wild-type meningococcal fHbp comprising SEQ ID NO: 1 [NB: it may elicit some antibodies which recognise both SEQ ID NOs: 1 and 4].

(b) it elicits antibodies in a mouse which are not bactericidal against strain MC58 in a serum bactericidal assay; for example, providing a serum bactericidal titer of ≤1:4 using the Goldschneider assay with human complement [11-13], and/or providing a serum bactericidal titer of ≤1:128 using baby rabbit complement.

(c) it has at least 75% sequence identity to both of SEQ ID NO: 1 and SEQ ID NO: 23, but it has a higher sequence identity to SEQ ID NO: 23 than to SEQ ID NO: 1, when aligned using the same algorithm and parameters.

(d) it includes one or more of the 6-mers listed as SEQ ID NOs: 38 to 48. NB: the 6-mers of SEQ ID NOs: 38 to 45 may overlap in the sequence, and the 6-mers of SEQ ID NOs: 47 & 48 may overlap in the sequence.

(e) when aligned with SEQ ID NO: 1, it has a threonine residue at the amino acid residue which aligns with Ala-2 of SEQ ID NO:1.

(f) when aligned with SEQ ID NO: 1, it has a valine residue at the amino acid residue which aligns with Gly-141 of SEQ ID NO:1.

Of these six criteria, a sequence preferably meets at least criterion (a) or (c), more preferably at least (a) & (c), even more preferably at least (a), (b) & (c), and most preferably all six.

For the second aspect of the invention, the second fHbp antigen comprises an amino acid sequence (i) having at least w % sequence identity to SEQ ID NO: 25 and/or (ii) consisting of a fragment of at least x contiguous amino acids from SEQ ID NO: 25. The value of w is at least 94 (e.g. 95, 96, 97, 98, 99 or more). The value of x is either (a) at least 50 e.g. 55, 60, 65, 70, 75, 80, 85, 90, 95, 100, 110, 120, 130, 140, 150, 160, 180, 200 or (b) at least 7 (e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200), provided that the fragment is not also a fragment of SEQ ID NO: 2 and/or of SEQ ID NO: 3. Preferred fragments comprise an epitope from SEQ ID NO: 25.

fHbp sequences which are more closely related to MC58 than to M01573, or vice versa, or which comprise a sequence with ≥94% identity to and/or a fragment of SEQ ID NO: 25, can be designed based on these known sequences, or they can be selected from the large number of wild-type fHbp sequences which have been reported in the art e.g. see references 1-8 and 14-19.

Suitable amino acid sequences used with the invention may, compared to SEQ ID NOs: 1 and 23, include one or more (e.g. 1, 2, 3, 4, 5, 6, 7, 8, 9, 10, etc.) conservative amino acid replacements i.e. replacements of one amino acid with another which has a related side chain. Genetically-encoded amino acids are generally divided into four families: (1) acidic i.e. aspartate, glutamate; (2) basic i.e. lysine, arginine, histidine; (3) non-polar i.e. alanine, valine, leucine, isoleucine, proline, phenylalanine, methionine, tryptophan; and (4) uncharged polar i.e. glycine, asparagine, glutamine, cysteine, serine, threonine, tyrosine. Phenylalanine, tryptophan, and tyrosine are sometimes classified jointly as aromatic amino acids. In general, substitution of single amino acids within these families does not have a major effect on the biological activity. The antigens may have one or more (e.g. 1, 2, 3, 4, 5, 6, 7, 8, 9, 10, etc.) single amino acid deletions relative to a reference sequence. The antigens may also include one or more (e.g. 1, 2, 3, 4, 5, 6, 7, 8, 9, 10, etc.) insertions (e.g. each of 1, 2, 3, 4 or 5 amino acids) relative to a reference sequence.

A composition of the invention can include only two different fHbp sequences, or can include more than two different fHbp sequences. For example, a composition of the first aspect may or may not include further fHbp sequences beyond the two fHbp sequences discussed above e.g. it may include a fHbp sequence from family II and/or from family III e.g. SEQ ID NO: 2 and/or SEQ ID NO: 3 herein. Thus a composition may be a bivalent fHbp composition, or may include be more than two different fHbp sequences e.g. in a trivalent or tetravalent fHbp composition.

A composition of the first aspect comprises two family I fHbp sequences, and ideally also includes a fHbp sequence from family II and/or family III. Usefully, it includes a fHbp antigen comprising an amino acid sequence (i) having at least w % sequence identity to SEQ ID NO: 25 and/or (ii) consisting of a fragment of at least x contiguous amino acids from SEQ ID NO: 25. The values of w and x are given above, and preferred fragments comprise an epitope from SEQ ID NO: 25. Such fHbp antigens (also present in compositions of the second aspect) may elicit antibodies in a mouse which are bactericidal against strain 961-5945 in a serum bactericidal assay; for example, providing a serum bactericidal titer of ≥1:4 using the Goldschneider assay with human complement [11-13], and/or providing a serum bactericidal titer of ≥1:128 using baby rabbit complement. Strain 961-5945 has been widely reported in the literature (e.g. see refs. 1, 2 & 20-26) and is available as isolate MDU 9615945, id 1002, from the *Neisseria* PubMLST collection. It is a B:2b:P1.21,16 strain with electrophoretic type A4 and MLST type 153. Its fHbp sequence is given in reference 23, GI:106073476.

Thus a composition of the first aspect may comprise (i) first and second fHbp antigens as defined above, and (ii) a third fHbp antigen comprising an amino acid sequence (i) having at least w % sequence identity to SEQ ID NO: 25 and/or (ii) consisting of a fragment of at least x contiguous amino acids from SEQ ID NO: 25.

A composition of the second aspect comprises two different fHbp antigens as disclosed above. The composition may include a third fHbp antigen, but anyway it is preferred that the composition does not include (i) an antigen comprising an amino acid sequence which has >95% sequence identity to SEQ ID NO: 23 or (ii) an antigen comprising an amino acid sequence which has >95% sequence identity to SEQ ID NO: 24.

A fHbp antigen in a composition of the invention may be lipidated e.g. at a N-terminus cysteine. In other embodiments, however, fHbp antigen(s) are not lipidated. For lipidated fHbps, lipids attached to cysteines will usually include palmitoyl residues e.g. as tripalmitoyl-S-glyceryl-cysteine (Pam3Cys), dipalmitoyl-S-glyceryl cysteine (Pam2Cys), N-acetyl (dipalmitoyl-S-glyceryl cysteine), etc. Examples of mature lipidated fHbp sequences are SEQ ID NO: 23 (including SEQ ID NO: 4), SEQ ID NO: 24 (including SEQ ID NO: 5), and SEQ ID NO: 25 (including SEQ ID NO: 6).

Where a composition comprises different meningococcal fHbp antigens, these may be present as separate polypeptides (e.g. a first and second polypeptide) or they may be present as part of a single 'hybrid' polypeptide i.e. where at least two (e.g. 2, 3, 4, 5, or more) fHbp antigens are expressed as a single polypeptide chain (fusion protein), as disclosed for meningococcal antigens in reference 27.

Hybrid polypeptides can be represented by the formula $NH_2$-A-{-X-L-}$_n$-B-COOH, wherein: each X is an amino acid sequence of a different fHbp antigen as defined above; L is an optional linker amino acid sequence; A is an optional N-terminal amino acid sequence; B is an optional C-terminal amino acid sequence; n is an integer of 2 or more (e.g. 2, 3, 4, 5, 6, etc.). Usually n is 2 or 3.

If a -X- moiety has a leader peptide sequence in its wild-type form, this may be included or omitted in the hybrid protein. In some embodiments, the leader peptides will be deleted except for that of the -X- moiety located at the N-terminus of the hybrid protein i.e. the leader peptide of $X_1$ will be retained, but the leader peptides of $X_2 \ldots X_n$ will be omitted. This is equivalent to deleting all leader peptides and using the leader peptide of $X_1$ as moiety -A-.

For each n instances of {-X-L-}, linker amino acid sequence -L- may be present or absent. For instance, when n=2 the hybrid may be $NH_2$-$X_1$-$L_1$-$X_2$-$L_2$-COOH, $NH_2$-$X_1$-$X_2$-COOH, $NH_2$-$X_1$-$L_1$-$X_2$-COOH, $NH_2$-$X_1$-$X_2$-$L_2$-COOH, etc. Linker amino acid sequence(s) -L- will typically be short (e.g. 20 or fewer amino acids i.e. 20, 19, 18, 17, 16, 15, 14, 13, 12, 11, 10, 9, 8, 7, 6, 5, 4, 3, 2, 1). Examples comprise short peptide sequences which facilitate cloning, poly-glycine linkers (i.e. comprising Gly$_n$ where n=2, 3, 4, 5, 6, 7, 8, 9, 10 or more), and histidine tags (i.e. His$_n$ where n=3, 4, 5, 6, 7, 8, 9, 10 or more). Other suitable linker amino acid sequences will be apparent to those skilled in the art. A useful linker is GSGGGG (SEQ ID NO: 15) or GSGSGGGG (SEQ ID NO:16), with the Gly-Ser dipeptide being formed from a BamHI restriction site, thus aiding cloning and manipulation, and the (Gly)$_4$ tetrapeptide being a typical poly-glycine linker. Another suitable linker, particularly for use as the final $L_n$ is a Leu-Glu dipeptide.

-A- is an optional N-terminal amino acid sequence. This will typically be short (e.g. 40 or fewer amino acids i.e. 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking, or short peptide sequences which facilitate cloning or purification (e.g. histidine tags i.e. His$_n$ where n=3, 4, 5, 6, 7, 8, 9, 10 or more). Other suitable N-terminal amino acid sequences will be apparent to those skilled in the art. If $X_1$ lacks its own N-terminus methionine, -A- is preferably an oligopeptide (e.g. with 1, 2, 3, 4, 5, 6, 7 or 8 amino acids) which provides a N-terminus methionine e.g. Met-Ala-Ser, or a single Met residue.

-B- is an optional C-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short peptide sequences which facilitate cloning or purification (e.g. comprising histidine tags i.e. His$_n$ where n=3, 4, 5, 6, 7, 8, 9, 10 or more, such as SEQ ID NO: 17), or sequences which enhance protein stability. Other suitable C-terminal amino acid sequences will be apparent to those skilled in the art.

Preferred compositions of the first and second aspects include a fHbp antigen comprising an amino acid sequence having at least 99% sequence identity (e.g. 100% identity) to SEQ ID NO: 25. This can be a third antigen in the first aspect and a second antigen in the second aspect. This antigen can be a lipoprotein with a N-terminal cysteine.

Adjuvants

As mentioned above, compositions of the invention are adjuvanted. The compositions include the adjuvant known as aluminium phosphate. This name is conventional, but is used for convenience only, as it is not a precise description of the actual chemical compound which is present (e.g. see chapter 9 of reference 28). The invention can use any of the "phosphate" adjuvants that are in general use.

The adjuvants known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt. Aluminium phosphates generally have a $PO_4$/Al molar ratio between 0.3 and 1.2. Aluminium phosphates can be distinguished from strict $AlPO_4$ by the presence of hydroxyl groups. For example, an IR spectrum band at 3164 cm$^{-1}$ (e.g. when heated to 200° C.) indicates the presence of structural hydroxyls. The aluminium phosphate adjuvant may contain a small amount of sulfate (i.e. aluminium hydroxyphosphate sulfate) and may also include sodium and/or chloride ions [29]. The adjuvant may be obtained by precipitation.

Aluminium hydroxyphosphate is not a stoichiometric compound and its hydroxyl and phosphate composition depends on precipitation reactants and conditions. This hydroxyl/phosphate composition affects the adjuvant's point of zero charge (PZC; the pH at which a surface has zero net charge). The PZC is inversely related to the degree of substitution of phosphate for hydroxyl (the P/Al molar ratio). Substitution of phosphate anions for hydroxyl anions lowers the PZC. Thus the PZC can be altered by changing the concentration of free phosphate ions in solution (more phosphate=more acidic PZC) or by adding a buffer such as a histidine buffer (makes PZC more basic). Aluminium phosphates used with the invention generally have a PZC of between 5.0 and 6.6 e.g. between 5.4 and 6.2.

The P/Al molar ratio of an aluminium phosphate adjuvant will generally be between 0.3 and 1.2, preferably between 0.8 and 1.2, or between 0.85 and 1.0, and more preferably about 0.9. A P/Al molar ratio of at least 0.5 can provide an adjuvant with better aging properties.

The aluminium phosphate will generally be amorphous (i.e. amorphous to X-rays). It will generally be particulate (e.g. plate-like morphology as seen in transmission electron micrographs). Typical diameters of the plates are 10-100 nm, and these form aggregates sized 0.5-20 μm (e.g. about 1-10 μm). Adsorptive capacities of between 0.7-1.5 mg protein per mg $Al^{+++}$ at pH 7.4 have been reported for aluminium phosphate adjuvants.

A typical adjuvant is amorphous aluminium hydroxyphosphate with P/Al molar ratio between 0.84 and 0.92, and this adjuvant may be included at 0.6 mg $Al^{3+}$/ml.

The concentration of $Al^{+++}$ in a composition for administration to a patient is preferably less than 5 mg/ml e.g. ≤4 mg/ml, ≤3 mg/ml, ≤2 mg/ml, ≤1 mg/ml, etc. A preferred range is between 0.2 and 1 mg/ml. A maximum $Al^{+++}$ concentration of 0.85 mg/dose is preferred.

It is known to use mixtures of different aluminium salts in a single vaccine e.g. see reference 30. Although adjuvants including both aluminium phosphate and hydroxide can be used with fHbp, it is preferred that a composition should not include any aluminium hydroxide adjuvant because, as described above, it can degrade certain antigens which may be admixed with the fHbp (in particular, conjugated bacterial capsular saccharides). Instead, it is preferred to use only an aluminium phosphate adjuvant.

When aluminium salt(s) is used as an adjuvant, at least 75% (by weight) of fHbp in a composition of the invention should be adsorbed to it/them e.g. ≥80%, ≥75% ≥90%, ≥95% or even 100%. The proportion of adsorbed fHbp can be controlled by altering salt concentration and/or pH during formulation e.g. in general, a higher NaCl concentration can decrease fHbp's adsorption. The amount of adsorption for any formulation will depend on a combination of parameters including the adjuvant's PZC, the salt concentration and pH during formulation, the adjuvant concentration, the antigen concentration and the antigen's pI. The impact of each of these parameters on adsorption can be readily assessed. The degree of adsorption can be determined by comparing the total amount of fHbp antigen in a composition (e.g. measured before adsorption occurs, or measured by desorbing adsorbed antigen) to the amount which remains in the supernatant after centrifugation (e.g. see chapter 4 of ref 31). The absence of detectable antigen in the supernatant after centrifugation indicates that total adsorption has occurred i.e. all of the fHbp is in the pellet, which contains the insoluble adjuvant and its adsorbed content. Efficient adsorption of fHbp antigens can use the techniques disclosed in reference 32.

Further Antigen(s)

In addition to fHbp antigen(s), compositions of the invention can include further antigens from meningococcus or from other pathogens e.g. from other bacteria such as pneumococcus.

Further Meningococcal Polypeptide Antigens

In addition to including meningococcal fHbp antigens, a composition may include one or more further meningococcal polypeptide antigen(s). Thus a composition may include a polypeptide antigen selected from the group consisting of: 287, NadA, NspA, HmbR, NhhA, App, and/or Omp85. These antigens will usefully be present as purified polypeptides e.g. recombinant polypeptides. The antigen will preferably elicit bactericidal anti-meningococcal antibodies after administration to a subject. If a composition includes a PorA antigen then, in some embodiments, only one meningococcal PorA serosubtype is included. In some embodiments, no meningococcal PorA outer membrane protein is included in a composition.

A composition of the invention may include a 287 antigen. The 287 antigen was included in the published genome sequence for meningococcal serogroup B strain MC58 [9] as gene NMB2132 (GenBank accession number GI:7227388; SEQ ID NO: 9 herein). The sequences of 287 antigen from many strains have been published since then. For example, allelic forms of 287 can be seen in FIGS. 5 and 15 of reference 33, and in example 13 and FIG. 21 of reference 34 (SEQ IDs 3179 to 3184 therein). Various immunogenic fragments of the 287 antigen have also been reported. Preferred 287 antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 9; and/or (b) comprising a fragment of at least 'n' consecutive amino acids of SEQ ID NO: 9, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 9. The most useful 287 antigens of the invention can elicit antibodies which, after administration to a subject, can bind to a meningococcal polypeptide consisting of amino acid sequence SEQ ID NO: 9. Advantageous 287 antigens for use with the invention can elicit bactericidal anti-meningococcal antibodies after administration to a subject.

A composition of the invention may include a NadA antigen. The NadA antigen was included in the published genome sequence for meningococcal serogroup B strain MC58 [9] as gene NMB1994 (GenBank accession number GI:7227256; SEQ ID NO: 10 herein). The sequences of NadA antigen from many strains have been published since then, and the protein's activity as a Neisserial adhesin has been well documented. Various immunogenic fragments of NadA have also been reported. Preferred NadA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 10; and/or (b) comprising a fragment of at least 'n' consecutive amino acids of SEQ ID NO: 10, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 10. The most useful NadA antigens of the invention can elicit antibodies which, after administration to a subject, can bind to a meningococcal polypeptide consisting of amino acid sequence SEQ ID NO: 10. Advantageous NadA antigens for use with the invention can elicit bactericidal anti-meningococcal antibodies after administration to a subject. A useful NadA antigen for use with the invention has amino acid sequence SEQ ID NO: 49.

A composition of the invention may include a NspA antigen. The NspA antigen was included in the published genome sequence for meningococcal serogroup B strain MC58 [9] as gene NMB0663 (GenBank accession number GI:7225888; SEQ ID NO: 11 herein). The antigen was previously known from references 35 & 36. The sequences of NspA antigen from many strains have been published since then. Various immunogenic fragments of NspA have also been reported. Preferred NspA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 11; and/or (b) comprising a fragment of at least 'n' consecutive amino acids of SEQ ID NO: 11, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 11. The most useful NspA antigens of the invention can elicit antibodies which, after administration to a subject, can bind to a meningococcal polypeptide consisting of amino acid sequence SEQ ID NO: 11. Advantageous NspA antigens for use with the invention can elicit bactericidal anti-meningococcal antibodies after administration to a subject.

Compositions of the invention may include a meningococcal HmbR antigen. The full-length HmbR sequence was included in the published genome sequence for meningococcal serogroup B strain MC58 [9] as gene NMB1668 (SEQ ID NO: 7 herein). Reference 37 reports a HmbR sequence from a different strain (SEQ ID NO: 8 herein). SEQ ID NOs: 7 and 8 differ in length by 1 amino acid and have 94.2% identity. The invention can use a polypeptide that comprises a full-length HmbR sequence, but it will often use a polypeptide that comprises a partial HmbR sequence. Thus in some embodiments a HmbR sequence used according to the invention may comprise an amino acid sequence having at least i % sequence identity to SEQ ID NO: 7, where the value of i is 50, 60, 70, 80, 90, 95, 99 or more. In other embodiments a HmbR sequence used according to the invention may comprise a fragment of at least j consecutive amino acids from SEQ ID NO: 7, where the value of j is 7, 8, 10, 12, 14, 16, 18, 20, 25, 30, 35, 40, 50, 60, 70, 80, 90, 100, 150, 200, 250 or more. In other embodiments a HmbR sequence used according to the invention may comprise an amino acid sequence (i) having at least i % sequence identity to SEQ ID NO: 7 and/or (ii) comprising a fragment of at least j consecutive amino acids from SEQ ID NO: 7. Preferred fragments of j amino acids comprise an epitope from SEQ ID NO: 7. Such epitopes will usually comprise amino acids that are located on the surface of HmbR. Useful epitopes include those with amino acids involved in HmbR's binding to haemoglobin, as antibodies that bind to these epitopes can block the ability of a bacterium to bind to host haemoglobin. The topology of HmbR, and its critical functional residues, were investigated in reference 38. The most useful HmbR antigens of the invention can elicit antibodies which, after administration to a subject, can bind to a meningococcal polypeptide consisting of amino acid sequence SEQ ID NO: 7. Advantageous HmbR antigens for use with the invention can elicit bactericidal anti-meningococcal antibodies after administration to a subject.

A composition of the invention may include a NhhA antigen. The NhhA antigen was included in the published genome sequence for meningococcal serogroup B strain MC58 [9] as gene NMB0992 (GenBank accession number GI:7226232; SEQ ID NO: 12 herein). The sequences of NhhA antigen from many strains have been published since e.g. refs 33 & 39, and various immunogenic fragments of NhhA have been reported. It is also known as Hsf. Preferred NhhA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 12; and/or (b) comprising a fragment of at least 'n' consecutive amino acids of SEQ ID NO: 12, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 12. The most useful NhhA antigens of the invention can elicit antibodies which, after administration to a subject, can bind to a meningococcal polypeptide consisting of amino acid sequence SEQ ID NO: 12. Advantageous NhhA antigens for use with the invention can elicit bactericidal anti-meningococcal antibodies after administration to a subject.

A composition of the invention may include an App antigen. The App antigen was included in the published genome sequence for meningococcal serogroup B strain MC58 [9] as gene NMB1985 (GenBank accession number GI:7227246; SEQ ID NO: 13 herein). The sequences of App antigen from many strains have been published since then. Various immunogenic fragments of App have also been reported. Preferred App antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 13; and/or (b) comprising a fragment of at least 'n' consecutive amino acids of SEQ ID NO: 13, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 13. The most useful App antigens of the invention can elicit antibodies which, after administration to a subject, can bind to a meningococcal polypeptide consisting of amino acid sequence SEQ ID NO: 13. Advantageous App antigens for use with the invention can elicit bactericidal anti-meningococcal antibodies after administration to a subject.

A composition of the invention may include an Omp85 antigen. The Omp85 antigen was included in the published genome sequence for meningococcal serogroup B strain MC58 [9] as gene NMB0182 (GenBank accession number GI:7225401; SEQ ID NO: 14 herein). The sequences of Omp85 antigen from many strains have been published since then. Further information on Omp85 can be found in references 40 and 41. Various immunogenic fragments of Omp85 have also been reported. Preferred Omp85 antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 14; and/or (b) comprising a fragment of at least 'n' consecutive amino acids of SEQ ID NO: 14, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 14. The most useful Omp85 antigens of the invention can elicit antibodies which, after administration to a subject, can bind to a meningococcal polypeptide consisting of amino acid sequence SEQ ID NO: 14. Advantageous Omp85 antigens for use with the invention can elicit bactericidal anti-meningococcal antibodies after administration to a subject.

Meningococcal Lipooligosaccharide

In addition to including meningococcal fHbp polypeptide antigen(s), a composition may include one or more meningococcal lipooligosaccharide (LOS) antigen(s). Meningococcal LOS is a glucosamine-based phospholipid that is found in the outer monolayer of the outer membrane of the bacterium. It includes a lipid A portion and a core oligosaccharide region, with the lipid A portion acting as a hydrophobic anchor in the membrane. Heterogeneity within the oligosaccharide core generates structural and antigenic diversity among different meningococcal strains, which has been used to subdivide the strains into 12 immunotypes (L1 to L12). The invention may use LOS from any immunotype e.g. from L1, L2, L3, L4, L5, L6, L7 and/or L8.

The L2 and L3 α-chains naturally include lacto-N-neotetraose (LNnT). Where the invention uses LOS from a L2 or L3 immunotype this LNnT may be absent. This absence can be achieved conveniently by using mutant strains that are engineered to disrupt their ability to synthesise the LNnT tetrasaccharide within the α-chain. It is known to achieve this goal by knockout of the enzymes that are responsible for the relevant biosynthetic additions [42,43]. For instance, knockout of the LgtB enzyme prevents addition of the terminal galactose of LNnT, as well as preventing downstream addition of the α-chain's terminal sialic acid. Knockout of the LgtA enzyme prevents addition of the N-acetylglucosamine of LNnT, and also the downstream additions. LgtA knockout may be accompanied by LgtC knockout. Similarly, knockout of the LgtE and/or GalE enzyme prevents addition of internal galactose, and knockout of LgtF prevents addition of glucose to the Hep$^I$ residue. Any of these knockouts can be used, singly or in combination, to disrupt the LNnT tetrasaccharide in a L2, L3, L4, L7 or L9 immunotype strain. Knockout of at least LgtB is preferred, as this provides a LOS that retains useful immunogenicity while removing the LNnT epitope.

In addition to, or in place of, mutations to disrupt the LNnT epitope, a knockout of the galE gene also provides a useful modified LOS, and a lipid A fatty transferase gene may similarly be knocked out [44]. At least one primary O-linked fatty acid may be removed from LOS [45]. LOS having a reduced number of secondary acyl chains per LOS molecule can also be used [46]. The LOS will typically include at least the GlcNAc-Hep$_2$phosphoethanolamine-KDO$_2$-Lipid A structure [47]. The LOS may include a GlcNAcβ1-3Galβ1-4Glc trisaccharide while lacking the LNnT tetrasaccharide.

LOS may be included in compositions of the invention in various forms. It may be used in purified form on its own. It may be conjugated to a carrier protein. When LOS is conjugated, conjugation may be via a lipid A portion in the LOS or by any other suitable moiety e.g. its KDO residues. If the lipid A moiety of LOS is absent then such alternative linking is required. Conjugation techniques for LOS are known from e.g. references 45, 47, 48, 49, etc. Useful carrier proteins for these conjugates are discussed below e.g. bacterial toxins, such as diphtheria or tetanus toxins, or toxoids or mutants thereof.

The LOS may be from a strain (e.g. a genetically-engineered meningococcal strain) which has a fixed (i.e. not phase variable) LOS immunotype as described in reference 50. For example, L2 and L3 LOS immunotypes may be fixed. Such strains may have a rate of switching between immunotypes that is reduced by more than 2-fold (even >50 fold) relative to the original wild-type strain. Reference 50 discloses how this result can be achieved by modification of the lgtA and/or lgtG gene products.

LOS may be O-acetylated on a GlcNac residue attached to its Heptose II residue e.g. for L3 [51].

An immunogenic composition can include more than one type of LOS e.g. LOS from meningococcal immunotypes L2 and L3. For example, the LOS combinations disclosed in reference 52 may be used.

A LOS antigen can preferably elicit bactericidal anti-meningococcal antibodies after administration to a subject.

However, preferred compositions of the invention are free from meningococcal lipooligosaccharide.

Meningococcal Capsular Saccharide Antigen(s)

In addition to including meningococcal fHbp antigens, a composition may include one or more meningococcal capsular saccharide conjugates. A composition of the invention may include one or more conjugates of capsular saccharides from 1, 2, 3, or 4 of meningococcal serogroups A, C, W135 and Y e.g. A+C, A+W135, A+Y, C+W135, C+Y, W135+Y, A+C+W135, A+C+Y, A+W135+Y, A+C+W135+Y, etc. Compositions including a conjugated serogroup C capsular saccharide are useful, and compositions including saccharides from all of serogroups A, C, W135 and Y are ideal.

The capsular saccharide of serogroup A meningococcus is a homopolymer of (α1→6)-linked N-acetyl-D-mannosamine-1-phosphate, with partial O-acetylation in the C3 and C4 positions. Acetylation at the C-3 position can be 70-95%. Conditions used to purify the saccharide can result in de-O-acetylation (e.g. under basic conditions), but it is useful to retain OAc at this C-3 position. In some embodiments, at least 50% (e.g. at least 60%, 70%, 80%, 90%, 95% or more) of the mannosamine residues in a serogroup A saccharides are O-acetylated at the C-3 position. Acetyl groups can be replaced with blocking groups to prevent hydrolysis [53], and such modified saccharides are still serogroup A saccharides within the meaning of the invention.

The serogroup C capsular saccharide is a homopolymer of (α2→9)-linked sialic acid (N-acetyl neuraminic acid, or 'NeuNAc'). The saccharide structure is written as →9)-Neu p NAc 7/8 OAc-(α2→. Most serogroup C strains have O-acetyl groups at C-7 and/or C-8 of the sialic acid residues, but about 15% of clinical isolates lack these O-acetyl groups [54,55]. The presence or absence of OAc groups generates unique epitopes, and the specificity of antibody binding to the saccharide may affect its bactericidal activity against O-acetylated (OAc+) and de-O-acetylated (OAc−) strains [56-58]. Serogroup C saccharides used with the invention may be prepared from either OAc+ or OAc− strains. Licensed MenC conjugate vaccines include both OAc− (NEISVAC-C™) and OAc+(MENJUGATE™ & MENINGITEC™) saccharides. In some embodiments, strains for production of serogroup C conjugates are OAc+ strains, e.g. of serotype 16, serosubtype P1.7a,1, etc. Thus C:16:P1.7a,1 OAc+ strains may be used. OAc+ strains in serosubtype P1.1 are also useful, such as the C11 strain.

The serogroup W135 saccharide is a polymer of sialic acid-galactose disaccharide units. Like the serogroup C saccharide, it has variable O-acetylation, but at sialic acid 7 and 9 positions [59]. The structure is written as: →4)-D-Neup5Ac(7/9OAc)-α-(2→6)-D-Gal-α-(1→.

The serogroup Y saccharide is similar to the serogroup W135 saccharide, except that the disaccharide repeating unit includes glucose instead of galactose. Like serogroup W135, it has variable O-acetylation at sialic acid 7 and 9 positions [59]. The serogroup Y structure is written as: →4)-D-Neup5Ac(7/9OAc)-α-(2→6)-D-Glc-α-(1→.

The saccharides used according to the invention may be O-acetylated as described above (e.g. with the same O-acetylation pattern as seen in native capsular saccharides), or they may be partially or totally de-O-acetylated at one or more positions of the saccharide rings, or they may be hyper-O-acetylated relative to the native capsular saccharides.

The saccharide moieties in conjugates may comprise full-length saccharides as prepared from meningococci, and/or may comprise fragments of full-length saccharides i.e. the saccharides may be shorter than the native capsular saccharides seen in bacteria. The saccharides may thus be depolymerised, with depolymerisation occurring during or after saccharide purification but before conjugation. Depolymerisation reduces the chain length of the saccharides. One depolymerisation method involves the use of hydrogen peroxide. Hydrogen peroxide is added to a saccharide (e.g. to give a final $H_2O_2$ concentration of 1%), and the mixture is then incubated (e.g. at about 55° C.) until a desired chain length reduction has been achieved. Another depolymerisation method involves acid hydrolysis. Other depolymerisation methods are known in the art. The saccharides used to prepare conjugates for use according to the invention may be obtainable by any of these depolymerisation methods. Depolymerisation can be used in order to provide an optimum chain length for immunogenicity and/or to reduce chain length for physical manageability of the saccharides. In some embodiments, saccharides have the following range of average degrees of polymerisation (Dp): A=10-20; C=12-22; W135=15-25; Y=15-25. In terms of molecular weight, rather than Dp, useful ranges are, for all serogroups: <100 kDa; 5 kDa-75 kDa; 7 kDa-50 kDa; 8 kDa-35 kDa; 12 kDa-25 kDa; 15 kDa-22 kDa.

In some embodiments, the average molecular weight for saccharides from each of meningococcal serogroups A, C, W135 and Y may be more than 50 kDa e.g. ≥75 kDa, ≥100 kDa, ≥110 kDa, ≥120 kDa, ≥130 kDa, etc. [60], and even up to 1500 kDa, in particular as determined by MALLS. For instance: a MenA saccharide may be in the range 50-500 kDa e.g. 60-80 kDa; a MenC saccharide may be in the range 100-210 kDa; a MenW135 saccharide may be in the range 60-190 kDa e.g. 120-140 kDa; and/or a MenY saccharide may be in the range 60-190 kDa e.g. 150-160 kDa.

The mass of meningococcal saccharide per serogroup in a composition will usually be between 1 µg and 20 µg e.g. between 2 and 10 µg per serogroup, or about 4 µg or about 5 µg or about 10 µg. Where conjugates from more than one serogroup are included then they may be present at substantially equal masses e.g. the mass of each serogroup's saccharide is within +10% of each other. As an alternative to an equal ratio, a double mass of serogroup A saccharide may be used. Thus a vaccine may include MenA saccharide at 10 µg and MenC, W135 and Y saccharides at 5 µg each.

Useful carrier proteins for meningococcal conjugates include bacterial toxins, such as diphtheria or tetanus toxins, or toxoids or mutants thereof. These are commonly used in conjugate vaccines. For example, the CRM197 diphtheria toxin mutant is useful [61]. Other suitable carrier proteins include synthetic peptides [62,63], heat shock proteins [64, 65], pertussis proteins [66,67], cytokines [68], lymphokines [68], hormones [68], growth factors [68], artificial proteins comprising multiple human CD4$^+$ T cell epitopes from various pathogen-derived antigens [69] such as N19 [70], protein D from *H. influenzae* [71-73], pneumolysin [74] or its non-toxic derivatives [75], pneumococcal surface protein PspA [76], iron-uptake proteins [77], toxin A or B from *C. difficile* [78], recombinant *Pseudomonas aeruginosa* exoprotein A (rEPA) [79], etc. CRM197 is preferred.

Where a composition includes conjugates from more than one meningococcal serogroup it is possible to use the same carrier protein for each separate conjugate, or to use different carrier proteins. In both cases, though, a mixture of different conjugates will usually be formed by preparing each serotype conjugate separately, and then mixing them to form a mixture of separate conjugates.

Conjugates with a saccharide:protein ratio (w/w) of between 1:5 (i.e. excess protein) and 5:1 (i.e. excess saccharide) may be used e.g. ratios between 1:2 and 5:1 and ratios between 1:1.25 and 1:2.5.

As described in reference 80, different meningococcal serogroup conjugates in a mixture can have different saccharide:protein ratios e.g. one may have a ratio of between 1:2 & 1:5, whereas another has a ratio between 5:1 & 1:1.99.

A carrier protein may be covalently conjugated to a meningococcal saccharide directly or via a linker. Various linkers are known. For example, attachment may be via a carbonyl, which may be formed by reaction of a free hydroxyl group of a modified saccharide with CDI [81,82] followed by reaction with a protein to form a carbamate linkage. Carbodiimide condensation can be used [83]. An adipic acid linker can be used, which may be formed by coupling a free —NH$_2$ group (e.g. introduced to a saccharide by amination) with adipic acid (using, for example, diimide activation), and then coupling a protein to the resulting saccharide-adipic acid intermediate [84,85]. Other linkers include β-propionamido [86], nitrophenyl-ethylamine [87], haloacyl halides [88], glycosidic linkages [89], 6-aminocaproic acid [90], N-succinimidyl-3-(2-pyridyldithio)-propionate (SPDP) [91], adipic acid dihydrazide ADH [92], $C_4$ to $C_{12}$ moieties [93], etc.

Conjugation via reductive amination can be used. The saccharide may first be oxidised with periodate to introduce an aldehyde group, which can then form a direct covalent linkage to a carrier protein via reductive amination e.g. to the ε-amino group of a lysine. If the saccharide includes multiple aldehyde groups per molecule then this linkage technique can lead to a cross-linked product, where multiple aldehydes react with multiple carrier amines.

As described in reference 94, a mixture can include one conjugate with direct saccharide/protein linkage and another conjugate with linkage via a linker. This arrangement applies particularly when using saccharide conjugates from different meningococcal serogroups e.g. MenA and MenC saccharides may be conjugated via a linker, whereas MenW135 and MenY saccharides may be conjugated directly to a carrier protein.

A meningococcal saccharide may comprise a full-length intact saccharide as prepared from meningococcus, and/or may comprise fragments of full-length saccharides i.e. the saccharides may be shorter than the native capsular saccharides seen in bacteria. The saccharides may thus be depolymerised, with depolymerisation occurring during or after saccharide purification but before conjugation. Depolymerisation reduces the chain length of the saccharides. Depolymerisation can be used in order to provide an optimum chain length for immunogenicity and/or to reduce chain length for physical manageability of the saccharides.

Conjugated Pneumococcal Capsular Saccharide(s)

Compositions of the invention may include a pneumococcal capsular saccharide conjugated to a carrier protein.

The invention can include capsular saccharide from one or more different pneumococcal serotypes. Where a composition includes saccharide antigens from more than one serotype, these are preferably prepared separately, conjugated separately, and then combined. Methods for purifying pneumococcal capsular saccharides are known in the art (e.g. see reference 95) and vaccines based on purified saccharides from 23 different serotypes have been known for many years. Improvements to these methods have also been described e.g. for serotype 3 as described in reference 96, or for serotypes 1, 4, 5, 6A, 6B, 7F and 19A as described in reference 97.

Pneumococcal capsular saccharide(s) will typically be selected from the following serotypes: 1, 2, 3, 4, 5, 6A, 6B, 7F, 8, 9N, 9V, 10A, 11A, 12F, 14, 15B, 17F, 18C, 19A, 19F, 20, 22F, 23F and/or 33F. Thus, in total, a composition may include a capsular saccharide from 1, 2, 3, 4, 5, 6, 7, 8, 9, 10, 11, 12, 13, 14, 15, 16, 17, 18, 19, 20, 21, 22, 23 or more different serotypes.

A useful combination of serotypes is a 7-valent combination e.g. including capsular saccharide from each of serotypes 4, 6B, 9V, 14, 18C, 19F, and 23F. Another useful combination is a 9-valent combination e.g. including capsular saccharide from each of serotypes 1, 4, 5, 6B, 9V, 14, 18C, 19F and 23F. Another useful combination is a 10-valent combination e.g. including capsular saccharide from each of serotypes 1, 4, 5, 6B, 7F, 9V, 14, 18C, 19F and 23F. An 11-valent combination may further include saccharide from serotype 3. A 12-valent combination may add to the 10-valent mixture: serotypes 6A and 19A; 6A and 22F; 19A and 22F; 6A and 15B; 19A and 15B; or 22F and 15B. A 13-valent combination may add to the 11-valent mixture: serotypes 19A and 22F; 8 and 12F; 8 and 15B; 8 and 19A; 8 and 22F; 12F and 15B; 12F and 19A; 12F and 22F; 15B and 19A; 15B and 22F; 6A and 19A, etc.

Thus a useful 13-valent combination includes capsular saccharide from serotypes 1, 3, 4, 5, 6A, 6B, 7F, 9V, 14, 18C, 19, 19F and 23F e.g. prepared as disclosed in references 98 to 101. One such combination includes serotype 6B saccharide at about 8 µg/ml and the other 12 saccharides at concentrations of about 4 µg/ml each. Another such combination includes serotype 6A and 6B saccharides at about 8 µg/ml each and the other 11 saccharides at about 4 µg/ml each.

Suitable carrier proteins for conjugates are discussed above in relation to meningococcal conjugates. Particularly useful carrier proteins for pneumococcal conjugate vaccines are CRM197, tetanus toxoid, diphtheria toxoid and *H. influenzae* protein D. CRM197 is used in PREVNAR™. A 13-valent mixture may use CRM197 as the carrier protein for each of the 13 conjugates, and CRM197 may be present at about 55-60 µg/ml.

Where a composition includes conjugates from more than one pneumococcal serotype, it is possible to use the same carrier protein for each separate conjugate, or to use different carrier proteins. In both cases, though, a mixture of different conjugates will usually be formed by preparing each serotype conjugate separately, and then mixing them to form a mixture of separate conjugates. Reference 102 describes potential advantages when using different carrier proteins in multivalent pneumococcal conjugate vaccines, but the PREVNAR™ product successfully uses the same carrier for each of seven different serotypes.

A carrier protein may be covalently conjugated to a pneumococcal saccharide directly or via a linker, as discussed above in relation to meningococcal conjugates. Cross-linking conjugation techniques are particularly useful for at least pneumococcal serotypes 4, 6B, 9V, 14, 18C, 19F and 23F.

As discussed above for meningococcal saccharides, a pneumococcal saccharide may comprise a full-length intact saccharide as prepared from pneumococcus, and/or may comprise fragments of full-length saccharides. Where more than one pneumococcal serotype is used then it is possible to use intact saccharides for each serotype, fragments for each serotype, or to use intact saccharides for some serotypes and fragments for other serotypes. Where a composition includes saccharide from any of serotypes 4, 6B, 9V, 14, 19F and 23F, these saccharides are preferably intact. In contrast, where a composition includes serotype 18C saccharide it is preferably depolymerised.

A serotype 3 saccharide may also be depolymerised, For instance, a serotype 3 saccharide can be subjected to acid hydrolysis for depolymerisation [98] e.g. using acetic acid. The resulting fragments may then be oxidised for activation (e.g. periodate oxidation, maybe in the presence of bivalent cations e.g. with $MgCl_2$), conjugated to a carrier (e.g. CRM197) under reducing conditions (e.g. using sodium cyanoborohydride), and then (optionally) any unreacted aldehydes in the saccharide can be capped (e.g. using sodium borohydride) [98]. Conjugation may be performed on lyophilized material e.g. after co-lyophilizing activated saccharide and carrier.

A serotype 1 saccharide may be at least partially de-O-acetylated e.g. achieved by alkaline pH buffer treatment [99] such as by using a bicarbonate/carbonate buffer. Such (partially) de-O-acetylated saccharides can be oxidised for activation (e.g. periodate oxidation), conjugated to a carrier (e.g. CRM197) under reducing conditions (e.g. using sodium cyanoborohydride), and then (optionally) any unreacted aldehydes in the saccharide can be capped (e.g. using sodium borohydride) [99]. Conjugation may be performed on lyophilized material e.g. after co-lyophilizing activated saccharide and carrier.

A serotype 19A saccharide may be oxidised for activation (e.g. periodate oxidation), conjugated to a carrier (e.g. CRM197) in DMSO under reducing conditions, and then (optionally) any unreacted aldehydes in the saccharide can be capped (e.g. using sodium borohydride) [103]. Conjugation may be performed on lyophilized material e.g. after co-lyophilizing activated saccharide and carrier.

Pneumococcal conjugates can ideally elicit anticapsular antibodies that bind to the relevant saccharide e.g. elicit an anti-saccharide antibody level ≥0.20 µg/mL [104]. The antibodies may be evaluated by enzyme immunoassay (EIA) and/or measurement of opsonophagocytic activity (OPA). The EIA method has been extensively validated and there is a link between antibody concentration and vaccine efficacy.

Further Antigens from Other Pathogen(s)

Compositions of the invention can include antigen(s) from further pathogen(s). For example, the composition may comprise one or more of the following further antigen(s):

an antigen from hepatitis B virus, such as the surface antigen HBsAg.

an antigen from *Bordetella pertussis*, such as pertussis holotoxin (PT) and filamentous haemagglutinin (FHA) from *B. pertussis*, optionally also in combination with pertactin and/or agglutinogens 2 and 3.

a diphtheria antigen, such as a diphtheria toxoid.

a tetanus antigen, such as a tetanus toxoid.

a saccharide antigen from *Haemophilus influenzae* B (Hib), typically conjugated.

inactivated poliovirus antigen(s).

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens. DTP combinations are thus preferred.

Extemporaneous Preparation

The invention also provides a kit comprising: (i) a first component comprising fHbp antigens, as described above; and (ii) a second component comprising a non-meningococcal immunogen. The kit components can be mixed to give an immunogenic composition for administering to a patient to protect against multiple pathogens.

The invention also provides a method for preparing a combined vaccine, comprising a step of mixing: (i) a first component comprising fHbp antigens, as described above; and (ii) a second component comprising a non-meningococcal immunogen. The mixed material may then be administered to a patient. The second component may be lyophilised, such that an aqueous first component reconstitutes it.

Pharmaceutical Compositions

The invention is concerned with immunogenic compositions for administration to a patient. These compositions are pharmaceutically acceptable and will typically include a suitable carrier. A thorough discussion of pharmaceutically acceptable carriers is available in reference 105.

Effective dosage volumes can be routinely established, but a typical human unit dose of the composition has a volume of about 0.5 ml.

The total amount of a fHbp polypeptide in a unit dose will usually be between 1 and 500 µg/dose e.g. between 60 and 200 µg/dose or between 120 and 500 µg/ml. An amount of 20, 40, 50, 60, 80, 100 or 200 µg for each fHbp antigen is typical in a human vaccine dose. Thus a vaccine may be formulated to include this amount of each fHbp.

The pH of a composition of the invention is usually between 6 and 8, and more preferably between 6.5 and 7.5 (e.g. about 7). As already discussed above, compositions may include a buffer e.g. a Tris buffer, a citrate buffer, a succinate buffer (such as a sodium succinate buffer), or a histidine buffer.

The composition may be sterile and/or pyrogen-free. Compositions of the invention may be isotonic with respect to humans.

Compositions of the invention may include sodium salts (e.g. sodium chloride) to give tonicity. A concentration of 10±2 mg/ml NaCl is typical e.g. about 9 mg/ml.

Compositions of the invention for administration to patients are immunogenic, and are more preferably vaccine compositions. Vaccines according to the invention may either be prophylactic (i.e. to prevent infection) or therapeutic (i.e. to treat infection), but will typically be prophylactic. Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. The antigen content of compositions of the invention will generally be expressed in terms of the amount of protein per dose.

Meningococci affect various areas of the body and so the compositions of the invention may be prepared in various liquid forms. For example, the compositions may be prepared as injectables, either as solutions or suspensions. The composition may be prepared for pulmonary administration e.g. by an inhaler, using a fine spray. The composition may be prepared for nasal, aural or ocular administration e.g. as spray or drops. Injectables for intramuscular administration are most typical.

Compositions of the invention may include an antimicrobial, particularly when packaged in multiple dose format. Antimicrobials such as thiomersal and 2-phenoxyethanol are commonly found in vaccines, but it is preferred to use either a mercury-free preservative or no preservative at all.

Compositions of the invention may comprise detergent e.g. a polysorbate (TWEEN), such as polysorbate 80. Detergents are generally present at low levels e.g. <0.01%, but higher levels have been suggested for stabilising antigen formulations [106] e.g. up to 10%. An example composition may include from 0.01 to 0.05% polysorbate, and this is particularly useful when using lipidated fHbp antigen(s).

Methods of Treatment

The invention also provides a method for raising an immune response in a mammal, comprising administering a composition of the invention to the mammal. The immune response is preferably protective against meningococcus and preferably involves antibodies. The method may raise a booster response in a patient that has already been primed.

The mammal is preferably a human. Where the vaccine is for prophylactic use, the human is preferably a child (e.g. a toddler or infant) or a teenager; where the vaccine is for therapeutic use, the human is preferably an adult. A vaccine intended for children may also be administered to adults e.g. to assess safety, dosage, immunogenicity, etc.

The invention also provides compositions of the invention for use as a medicament. The medicament is preferably used, as described above, to raise an immune response in a mammal (i.e. it is an immunogenic composition) and is more preferably a vaccine.

The invention also provides the use of at least two fHbp antigens, as defined above, in the manufacture of a medicament for raising an immune response, as described above, in a mammal.

These uses and methods are preferably for the prevention and/or treatment of a disease caused by N. meningitidis e.g. bacterial (or, more specifically, meningococcal) meningitis, or septicemia.

One way of checking efficacy of therapeutic treatment involves monitoring meningococcal infection after administration of the composition of the invention. One way of checking efficacy of prophylactic treatment involves monitoring immune responses against antigens after administration of the composition. Immunogenicity of compositions of the invention can be determined by administering them to test subjects (e.g. children 12-16 months age, or animal models) and then determining standard parameters including serum bactericidal antibodies (SBA) and ELISA titres (GMT) for meningococcus. These immune responses will generally be determined around 4 weeks after administration of the composition, and compared to values determined before administration of the composition. A SBA increase of at least 4-fold or 8-fold is preferred. Where more than one dose of the composition is administered, more than one post-administration determination may be made.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by any other suitable route. The invention may be used to elicit systemic and/or mucosal immunity. Intramuscular administration to the thigh or the upper arm is preferred. Injection may be via a needle (e.g. a hypodermic needle), but needle-free injection may alternatively be used. A typical intramuscular dose is 0.5 ml.

Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined.

General

The practice of the present invention will employ, unless otherwise indicated, conventional methods of chemistry, biochemistry, molecular biology, immunology and pharmacology, within the skill of the art. Such techniques are explained fully in the literature. See, e.g., references 107-113, etc.

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

Where the invention concerns an "epitope", this epitope may be a B-cell epitope and/or a T-cell epitope, but will usually be a B-cell epitope. Such epitopes can be identified empirically (e.g. using PEPSCAN [114,115] or similar methods), or they can be predicted (e.g. using the Jameson-Wolf antigenic index [116], matrix-based approaches [117], MAPITOPE [118], TEPITOPE [119,120], neural networks [121], OptiMer & EpiMer [122,123], ADEPT [124], Tsites [125], hydrophilicity [126], antigenic index [127] or the methods disclosed in references 128-132, etc.). Epitopes are the parts of an antigen that are recognised by and bind to the antigen binding sites of antibodies or T-cell receptors, and they may also be referred to as "antigenic determinants".

Where the invention uses a "purified" antigen, this antigen is separated from its naturally occurring environment. For example, the antigen will be substantially free from other meningococcal components, other than from any other purified antigens that are present. A mixture of purified antigens will typically be prepared by purifying each antigen separately and then re-combining them, even if the two antigens are naturally present in admixture.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of ref. 133. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in ref 134.

The word "substantially" does not exclude "completely" e.g. a composition which is "substantially free" from Y may be completely free from Y. Where necessary, the word "substantially" may be omitted from the definition of the invention.

"GI" numbering is used above. A GI number, or "GenInfo Identifier", is a series of digits assigned consecutively to each sequence record processed by NCBI when sequences are added to its databases. The GI number bears no resemblance to the accession number of the sequence record. When a sequence is updated (e.g. for correction, or to add more annotation or information) then it receives a new GI number. Thus the sequence associated with a given GI number is never changed.

MODES FOR CARRYING OUT THE INVENTION

Three fHbp proteins were used, representing the following strains and fHbp families:

|  | Strain | | |
|---|---|---|---|
|  | MC58 | M01573 | M01240320 |
| fHbp family | I | I | III |
| SEQ ID NO | 1/26 | 4/23 | 6/25 |

These were tested as monovalent vaccines or as bivalent vaccines (either as MC58+M01573 or MC58+M01240320).

Figure 1:
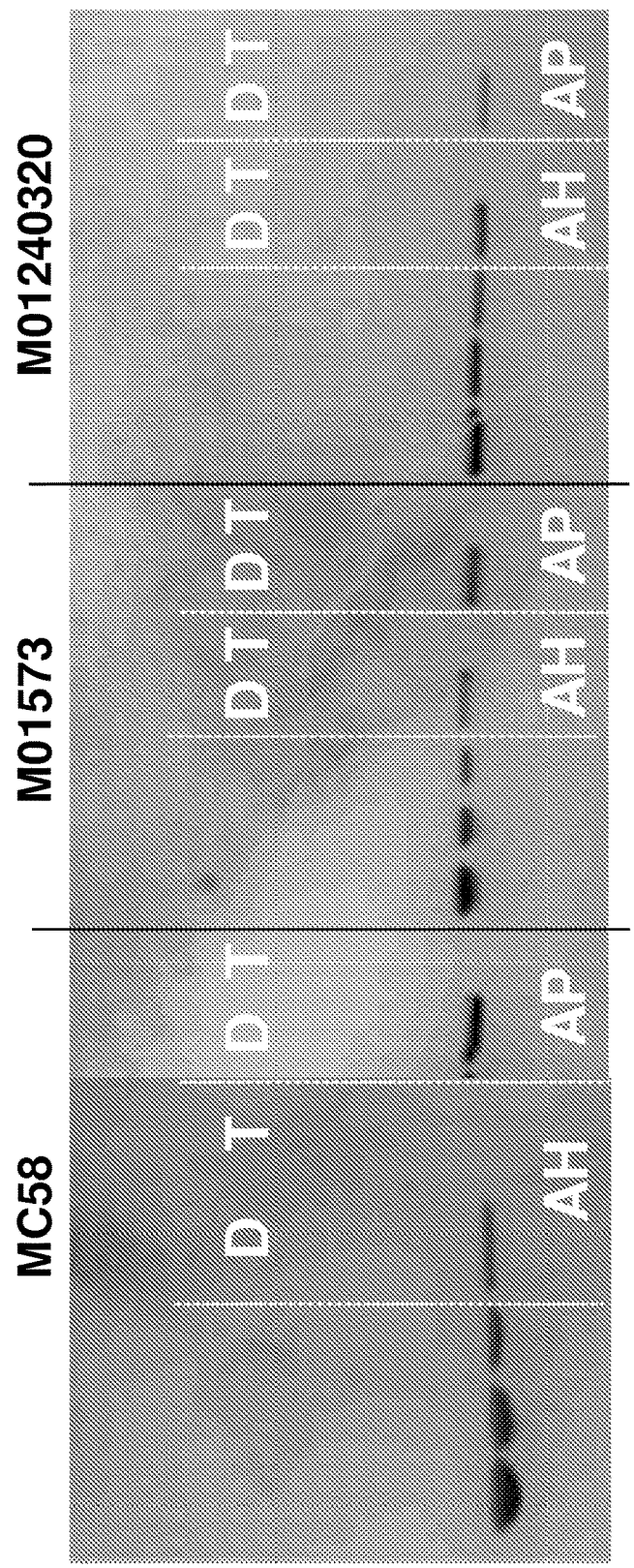
FIG. 1 shows adsorption of fHbp antigens to aluminium hydroxide (AH) or aluminium phosphate (AP) adjuvants. Lanes marked "D" are antigen after desorption treatment, whereas "T" lanes are the solution-phase antigens after adsorption. Thus a band in "D" but absent from "T" shows that the antigen is fully adsorbed to the adjuvant, but could be desorbed. The 3 lanes to the left of "D" are an antigen standard at 10%, 5% or 2.5% of the vaccine dose.
Figure 2:
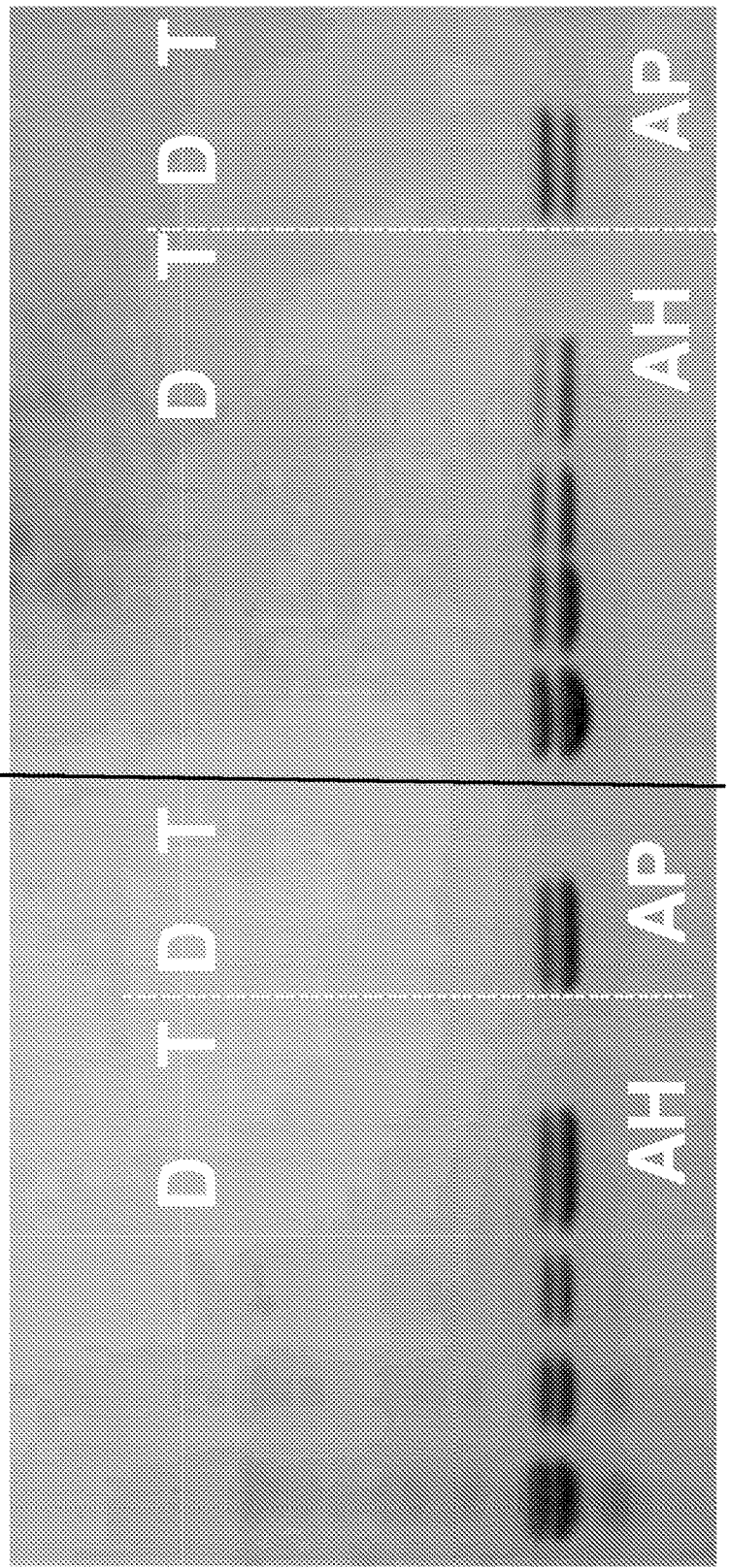
FIG. 2 is like FIG. 1, but shows adsorption of fHbp mixtures.

The antigens were adsorbed to an aluminium hydroxide adjuvant (AH) or to an aluminium phosphate adjuvant (AP). FIG. 1 confirms that the individual fHbp antigens adsorbed well to both adjuvants, and could be desorbed intact. FIG. 2 shows that this result was also seen with the bivalent mixtures.

These monovalent and bivalent vaccines were also used to immunise mice and the resulting sera were tested for bactericidal activity against various meningococcal strains. The following table shows results against 2 strains from each of fHbp families I, II and III, where a "+" indicates a bactericidal titre of 128 or more:

| Strain name | MC58 | | M01573 | | MO1240320 | | MC58 + M01573 | | MC58 + M01240320 | |
|---|---|---|---|---|---|---|---|---|---|---|
| (fHbp family) | AH | AP | AH | AP | AH | AP | AH | AP | AH | AP |
| MC58 (I) | + | + | − | − | − | − | + | + | + | + |
| NZ98/254 (I) | − | − | − | − | − | − | + | + | + | − |
| 961-5945 (II) | − | − | − | − | + | − | − | − | + | + |

-continued

| Strain name | MC58 | | M01573 | | MO1240320 | | MC58 + M01573 | | MC58 + M01240320 | |
|---|---|---|---|---|---|---|---|---|---|---|
| (fHbp family) | AH | AP | AH | AP | AH | AP | AH | AP | AH | AP |
| M12566 (II) | − | − | − | − | + | − | − | − | + | + |
| M01240355 (III) | − | − | − | − | + | + | − | − | + | + |
| M01240320 (III) | − | − | − | − | + | + | − | − | + | + |

Therefore the MC58 antigen was able to protect against the homologous strain with both adjuvants, but not against the other strains. The M01240320 antigen was able to protect against the homologous strain with both adjuvants, and also against another family III strain, but did not protect against family I strains and could protect against family II strains when using an AH adjuvant. The M01573 antigen alone did not protect against any of these six strains, with either adjuvant. Thus results were mixed with the monovalent vaccines.

The bivalent vaccine based on a combination of MC58 and M01573 protected against both family I strains, even though neither of the antigens alone had protected against NZ98/254. This result was seen with both adjuvants. As expected, however, the mixture of two family I antigens did not afford protection against family II or family III strains.

The bivalent vaccine based on a combination of MC58 and M01240320 protected against all six strains (except for one strain when using the AP adjuvant), including family II strains.

Many circulating meningococcal strains are in fHbp family I, and a large proportion of these are in sub-family I.1 (represented by MC58). Thus the M01573 sequence alone is unsuitable for ensuring coverage of this large sub-family. Instead of relying only on M01573, therefore, a vaccine should either replace it, or supplement it with a second family I sequence e.g. M01573+MC58. A combination of a sub-family I.1 sequence with a family III sequence can give broad protection using either an AH or an AP adjuvant.

Alignment of SEQ ID NOs: 23 and 26

SEQ ID NOs: 23 and 26 are mature amino acid sequences (N-terminal cysteine) from strains MC58 and M01573, respectively. They align as follows:

```
SEQID_26  CSSGGGG-----VAADIGAGLADALTAPLDHKDKGLQSLTLDQSVRKNEKLKLAAQGAEK    55
SEQID_23  CSSGGGGSGGGGVTADIGTGLADALTAPLDHKDKGLKSLTLEDSISQNGTLTLSAQGAEK    60
          *******     *:****:*****************:****::*: :* .*.*:******

SEQID_26  TYGNGDSLNTGKLKNDKVSRFDFIRQIEVDGQLITLESGEFQVYKQSHSALTAFQTEQIQ   115
SEQID_23  TYGNGDSLNTGKLKNDKVSRFDFIRQIEVDGQLITLESGEFQVYKQSHSALTALQTEQEQ   120
          *****************************************************:**** *

SEQID_26  DSEHSGKMVAKRQFRIGDIAGEHTSFDKLPEGGRATYRGTAFGSDDAGGKLTYTIDFAAK   175
SEQID_23  DPEHSEKMVAKRRFRIGDIAGEHTSFDKLPKDVMATYRGTAFGSDDAGGKLTYTIDFAAK   180
          *.*** ******:*****************:. *************************

SEQID_26  QGNGKIEHLKSPELNVDLAAADIKPDGKRHAVISGSVLYNQAEKGSYSLGIFGGKAQEVA   235
SEQID_23  QGHGKIEHLKSPELNVDLAVAYIKPDEKHHAVISGSVLYNQDEKGSYSLGIFGEKAQEVA   240
          **:***************.* ****   *:************ ********** *****

SEQID_26  GSAEVKTVNGIRHIGLAAKQ                                          255
SEQID_23  GSAEVETANGIHHIGLAAKQ                                          260
          *****: *.***:*******
```

Starting from Val-8 of SEQ ID NO: 26 and Val-13 of SEQ ID NO: 23 (i.e. excluding the N-terminus repeat region), they are 87.5% identical (217/248 identical residues).

When aligned with sequences from MC58, 961-5945 and M1239, two residues are unique to SEQ ID NO: 23, namely Thr-14 and Val-153, which align with residues 2 and 141 of SEQ ID NO: 1.

It will be understood that the invention has been described by way of example only and modifications may be made whilst remaining within the scope and spirit of the invention.

REFERENCES

[1] Masignani et al. (2003) *J Exp Med* 197:789-799.
[2] Welsch et al. (2004) *J Immunol* 172:5606-15.
[3] Hou et al. (2005) *J Infect Dis* 192(4):580-90.
[4] WO03/063766.
[5] Fletcher et al. (2004) *Infect Immun* 72:2088-2100.
[6] Zhu et al. (2005) *Infect Immun* 73(10):6838-45.
[7] Cantini et al. (2006) *J. Biol. Chem.* 281:7220-7227
[8] WO2004/048404
[9] Tettelin et al. (2000) *Science* 287:1809-1815.
[10] Mascioni et al. (2009) *J. Biol Chem* 284:8738-46.
[11] Goldschneider et al. (1969) *J. Exp. Med.* 129:1307-26.
[12] Santos et al. (2001) *Clinical and Diagnostic Laboratory Immunology* 8:616-23.
[13] Frasch et al. (2009) *Vaccine* 27S:B112-6.
[14] WO2004/094596.
[15] WO2008/079372.
[16] WO03/020756.
[17] WO2006/024954.
[18] WO2007/060548.
[19] WO2009/104097.
[20] Comanducci et al. (2002) *J Exp Med* 195:1445-54.
[21] Dunning Hotopp et al. (2006) *Microbiol* 152:3733-49.
[22] Giuliani et al. (2005) *Infect Immun* 73:1151-60.
[23] Beernink et al. (2006) *Clin Vaccine Immunol* 13:758-63.
[24] Pajon et al. (2010) *Vaccine* 28:2122-9.
[25] Oriente et al. (2009) *J Bacteriol.* doi:10.1128/JB.01308-09

[26] Metruccio et al. (2009) *PLoS Pathog.* 5(12): e1000710.
[27] Giuliani et al. (2006) *PNAS USA* 103:10834-9.
[28] *Vaccine Design: The Subunit and Adjuvant Approach* (Powell & Newman) 1995 (ISBN 0-306-44867-X).
[29] Burrell et al. (2001) *Vaccine* 19:275-81.
[30] WO01/22992.
[31] *Methods in Molecular Medicine*, Vol. 42 (ed. O'Hagan) Vaccine Adjuvants . . . .
[32] PCT/IB2010/000733.
[33] WO00/66741.
[34] WO99/57280
[35] Martin et al. (1997) *J Exp Med* 185(7):1173-83.
[36] WO96/29412.
[37] U.S. Pat. No. 5,698,438.
[38] Perkins-Balding et al. (2003) *Microbiology* 149:3423-35.
[39] WO01/55182.
[40] WO01/38350.
[41] WO00/23595.
[42] Ram et al. (2003) *J Biol Chem* 278:50853-62.
[43] WO2004/014417.
[44] WO98/53851
[45] U.S. Pat. No. 6,531,131.
[46] WO00/26384.
[47] U.S. Pat. No. 6,645,503
[48] WO03/070282.
[49] WO94/08021
[50] WO2004/015099.
[51] WO2007/144316.
[52] WO2007/144317.
[53] WO03/080678.
[54] Glode et al. (1979) *J Infect Dis* 139:52-56
[55] WO94/05325; U.S. Pat. No. 5,425,946.
[56] Arakere & Frasch (1991) *Infect. Immun.* 59:4349-4356.
[57] Michon et al. (2000) *Dev. Biol.* 103:151-160.
[58] Rubinstein & Stein (1998) *J. Immunol.* 141:4357-4362.
[59] WO2005/033148
[60] WO2007/000314.
[61] *Research Disclosure*, 453077 (January 2002)
[62] EP-A-0378881.
[63] EP-A-0427347.
[64] WO93/17712
[65] WO94/03208.
[66] WO98/58668.
[67] EP-A-0471177.
[68] WO91/01146
[69] Falugi et al. (2001) *Eur J Immunol* 31:3816-3824.
[70] Baraldo et al. (2004) *Infect Immun* 72(8):4884-7.
[71] EP-A-0594610.
[72] Ruan et al. (1990) *J Immunol* 145:3379-3384.
[73] WO00/56360.
[74] Kuo et al. (1995) *Infect Immun* 63:2706-13.
[75] Michon et al. (1998) *Vaccine.* 16:1732-41.
[76] WO02/091998.
[77] WO01/72337
[78] WO00/61761.
[79] WO00/33882
[80] WO2007/000341.
[81] Bethell G. S. et al., *J. Biol. Chem.*, 1979, 254, 2572-4
[82] Hearn M. T. W., *J. Chromatogr.*, 1981, 218, 509-18
[83] WO2007/000343.
[84] *Mol. Immunol.*, 1985, 22, 907-919
[85] EP-A-0208375
[86] WO00/10599
[87] Gever et al., *Med. Microbiol. Immunol*, 165: 171-288 (1979).
[88] U.S. Pat. No. 4,057,685.
[89] U.S. Pat. Nos. 4,673,574; 4,761,283; 4,808,700.
[90] U.S. Pat. No. 4,459,286.
[91] U.S. Pat. No. 5,204,098
[92] U.S. Pat. No. 4,965,338
[93] U.S. Pat. No. 4,663,160.
[94] WO2007/000342.
[95] *WHO Technical Report Series* No. 927, 2005. Pages 64-98.
[96] US-2008/0102498.
[97] US-2006/0228381.
[98] US-2007/0231340.
[99] US-2007/0184072.
[100] US-2006/0228380.
[101] WO2008/143709.
[102] WO2007/071707
[103] US-2007/0184071.
[104] Jodar et al. (2003) *Vaccine* 21:3265-72.
[105] Gennaro (2000) *Remington: The Science and Practice of Pharmacy.* 20th edition, ISBN: 0683306472.
[106] WO2007/127665.
[107] *Methods In Enzymology* (S. Colowick and N. Kaplan, eds., Academic Press, Inc.)
[108] *Handbook of Experimental Immunology*, Vols. I-IV (D. M. Weir and C. C. Blackwell, eds, 1986, Blackwell Scientific Publications)
[109] Sambrook et al. (2001) *Molecular Cloning: A Laboratory Manual,* 3rd edition (Cold Spring Harbor Laboratory Press).
[110] *Handbook of Surface and Colloidal Chemistry* (Birdi, K. S. ed., CRC Press, 1997)
[111] Ausubel et al. (eds) (2002) *Short protocols in molecular biology,* 5th edition (Current Protocols).
[112] *Molecular Biology Techniques: An Intensive Laboratory Course,* (Ream et al., eds., 1998, Academic Press)
[113] *PCR (Introduction to Biotechniques Series),* 2nd ed. (Newton & Graham eds., 1997, Springer Verlag)
[114] Geysen et al. (1984) *PNAS USA* 81:3998-4002.
[115] Carter (1994) *Methods Mol Biol* 36:207-23.
[116] Jameson, B A et al. 1988, *CABIOS* 4(1):181-186.
[117] Raddrizzani & Hammer (2000) *Brief Bioinform* 1(2): 179-89.
[118] Bublil et al. (2007) *Proteins* 68(1):294-304.
[119] De Lalla et al. (1999) *J. Immunol.* 163:1725-29.
[120] Kwok et al. (2001) *Trends Immunol* 22:583-88.
[121] Brusic et al. (1998) *Bioinformatics* 14(2):121-30
[122] Meister et al. (1995) *Vaccine* 13(6):581-91.
[123] Roberts et al. (1996) *AIDS Res Hum Retroviruses* 12(7):593-610.
[124] Maksyutov & Zagrebelnaya (1993) *Comput Appl Biosci* 9(3):291-7.
[125] Feller & de la Cruz (1991) *Nature* 349(6311):720-1.
[126] Hopp (1993) *Peptide Research* 6:183-190.
[127] Welling et al. (1985) *FEBS Lett.* 188:215-218.
[128] Davenport et al. (1995) *Immunogenetics* 42:392-297.
[129] Tsurui & Takahashi (2007) *J Pharmacol Sci.* 105(4): 299-316.
[130] Tong et al. (2007) *Brief Bioinform.* 8(2):96-108.
[131] Schirle et al. (2001) *J Immunol Methods.* 257(1-2):1-16.
[132] Chen et al. (2007) *Amino Acids* 33(3):423-8.
[133] *Current Protocols in Molecular Biology* (F. M. Ausubel et al., eds., 1987) Supplement 30
[134] Smith & Waterman (1981) *Adv. Appl. Math.* 2: 482-489.

The invention claimed is:

1. An immunogenic composition comprising an immunologically effective amount of a first factor H binding protein (fHbp) antigen and an immunologically effective amount of a second fHbp antigen, present as two separate polypeptides, and an immunologically effective amount of an aluminium phosphate adjuvant, wherein:

the first fHbp antigen comprises an amino acid sequence wherein at least 90% of its amino acids are the same as both of SEQ ID NO: 26 and SEQ ID NO: 23, but wherein the percentage of amino acids that are the same as SEQ ID NO: 26 is higher than the percentage of amino acids that are the same as SEQ ID NO: 23, when aligned using the same algorithm and parameters; and the second fHbp antigen comprises an amino acid sequence wherein at least 94% of its amino acids are the same as SEQ ID NO: 25.

2. The composition of claim 1, wherein the composition does not comprise (i) an antigen comprising an amino acid sequence wherein more than 95% of its amino acids are the same as SEQ ID NO: 23, or (ii) an antigen comprising an amino acid sequence wherein more than 95% of its amino acids are the same as SEQ ID NO: 24.

3. The composition of claim 1, wherein at least one of the fHbp antigens is lipidated at a N terminus cysteine.

4. The composition of claim 1, further comprising a pneumococcal capsular saccharide conjugated to a carrier protein.

* * * * *

SEQUENCE LISTING

<160> NUMBER OF SEQ ID NOS: 49

<210> SEQ ID NO 1
<211> LENGTH: 248
<212> TYPE: PRT
<213> ORGANISM: Neisseria meningitidis

<400> SEQUENCE: 1

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
                20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
                100                 105                 110

Ser Gly Lys Met Val Ala Lys Arg Gln Phe Arg Ile Gly Asp Ile Ala
                115                 120                 125

Gly Glu His Thr Ser Phe Asp Lys Leu Pro Glu Gly Gly Arg Ala Thr
        130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Asp Leu Ala Ala Ala Asp Ile Lys
                180                 185                 190

Pro Asp Gly Lys Arg His Ala Val Ile Ser Gly Ser Val Leu Tyr Asn
            195                 200                 205

Gln Ala Glu Lys Gly Ser Tyr Ser Leu Gly Ile Phe Gly Gly Lys Ala
        210                 215                 220

Gln Glu Val Ala Gly Ser Ala Glu Val Lys Thr Val Asn Gly Ile Arg
225                 230                 235                 240

His Ile Gly Leu Ala Ala Lys Gln
                245

<210> SEQ ID NO 2
<211> LENGTH: 247
<212> TYPE: PRT
<213> ORGANISM: Neisseria meningitidis

<400> SEQUENCE: 2

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Ser
                20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln

```
                 65                  70                  75                  80
Leu Ile Thr Leu Glu Ser Gly Glu Phe Gln Ile Tyr Lys Gln Asp His
                 85                  90                  95

Ser Ala Val Ala Leu Gln Ile Glu Lys Ile Asn Asn Pro Asp Lys
                100                 105                 110

Ile Asp Ser Leu Ile Asn Gln Arg Ser Phe Leu Val Ser Gly Leu Gly
                115                 120                 125

Gly Glu His Thr Ala Phe Asn Gln Leu Pro Asp Gly Lys Ala Glu Tyr
            130                 135                 140

His Gly Lys Ala Phe Ser Ser Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
                180                 185                 190

Asp Glu Lys Ser His Ala Val Ile Leu Gly Asp Thr Arg Tyr Gly Ser
            195                 200                 205

Glu Glu Lys Gly Thr Tyr His Leu Ala Leu Phe Gly Asp Arg Ala Gln
        210                 215                 220

Glu Ile Ala Gly Ser Ala Thr Val Lys Ile Gly Glu Lys Val His Glu
225                 230                 235                 240

Ile Gly Ile Ala Gly Lys Gln
                245

<210> SEQ ID NO 3
<211> LENGTH: 250
<212> TYPE: PRT
<213> ORGANISM: Neisseria meningitidis

<400> SEQUENCE: 3

Val Ala Ala Asp Ile Gly Thr Gly Leu Ala Asp Ala Leu Thr Ala Pro
1               5                  10                  15

Leu Asp His Lys Asp Lys Gly Leu Lys Ser Leu Thr Leu Glu Asp Ser
                20                  25                  30

Ile Pro Gln Asn Gly Thr Leu Thr Leu Ser Ala Gln Gly Ala Glu Lys
                35                  40                  45

Thr Phe Lys Ala Gly Asp Lys Asp Asn Ser Leu Asn Thr Gly Lys Leu
        50                  55                  60

Lys Asn Asp Lys Ile Ser Arg Phe Asp Phe Val Gln Lys Ile Glu Val
65                  70                  75                  80

Asp Gly Gln Thr Ile Thr Leu Ala Ser Gly Glu Phe Gln Ile Tyr Lys
                85                  90                  95

Gln Asn His Ser Ala Val Val Ala Leu Gln Ile Glu Lys Ile Asn Asn
                100                 105                 110

Pro Asp Lys Thr Asp Ser Leu Ile Asn Gln Arg Ser Phe Leu Val Ser
            115                 120                 125

Gly Leu Gly Gly Glu His Thr Ala Phe Asn Gln Leu Pro Gly Gly Lys
130                 135                 140

Ala Glu Tyr His Gly Lys Ala Phe Ser Ser Asp Pro Asn Gly Arg
145                 150                 155                 160

Leu His Tyr Ser Ile Asp Phe Thr Lys Lys Gln Gly Tyr Gly Arg Ile
                165                 170                 175

Glu His Leu Lys Thr Leu Glu Gln Asn Val Glu Leu Ala Ala Ala Glu
                180                 185                 190
```

```
Leu Lys Ala Asp Glu Lys Ser His Ala Val Ile Leu Gly Asp Thr Arg
            195                 200                 205

Tyr Gly Ser Glu Glu Lys Gly Thr Tyr His Leu Ala Leu Phe Gly Asp
        210                 215                 220

Arg Ala Gln Glu Ile Ala Gly Ser Ala Thr Val Lys Ile Gly Glu Lys
225                 230                 235                 240

Val His Glu Ile Gly Ile Ala Gly Lys Gln
                245                 250

<210> SEQ ID NO 4
<211> LENGTH: 248
<212> TYPE: PRT
<213> ORGANISM: Neisseria meningitidis

<400> SEQUENCE: 4

Val Thr Ala Asp Ile Gly Thr Gly Leu Ala Asp Ala Leu Thr Ala Pro
1               5                   10                  15

Leu Asp His Lys Asp Lys Gly Leu Lys Ser Leu Thr Leu Glu Asp Ser
            20                  25                  30

Ile Ser Gln Asn Gly Thr Leu Thr Leu Ser Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Leu Gln Thr Glu Gln Glu Gln Asp Pro Glu His
            100                 105                 110

Ser Glu Lys Met Val Ala Lys Arg Arg Phe Arg Ile Gly Asp Ile Ala
        115                 120                 125

Gly Glu His Thr Ser Phe Asp Lys Leu Pro Lys Asp Val Met Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly His Gly Lys Ile Glu His
                165                 170                 175

Leu Lys Ser Pro Glu Leu Asn Val Asp Leu Ala Val Ala Tyr Ile Lys
            180                 185                 190

Pro Asp Glu Lys His His Ala Val Ile Ser Gly Ser Val Leu Tyr Asn
        195                 200                 205

Gln Asp Glu Lys Gly Ser Tyr Ser Leu Gly Ile Phe Gly Glu Lys Ala
    210                 215                 220

Gln Glu Val Ala Gly Ser Ala Glu Val Glu Thr Ala Asn Gly Ile His
225                 230                 235                 240

His Ile Gly Leu Ala Ala Lys Gln
                245

<210> SEQ ID NO 5
<211> LENGTH: 250
<212> TYPE: PRT
<213> ORGANISM: Neisseria meningitidis

<400> SEQUENCE: 5

Val Ala Ala Asp Ile Gly Ala Gly Leu Ala Asp Ala Leu Thr Ala Pro
1               5                   10                  15
```

```
Leu Asp His Lys Asp Lys Gly Leu Lys Ser Leu Thr Leu Glu Asp Ser
         20                  25                  30

Ile Ser Gln Asn Gly Thr Leu Thr Leu Ser Ala Gln Gly Ala Glu Arg
         35                  40                  45

Thr Phe Lys Ala Gly Asp Lys Asp Asn Ser Leu Asn Thr Gly Lys Leu
     50                  55                  60

Lys Asn Asp Lys Ile Ser Arg Phe Asp Phe Ile Arg Gln Ile Glu Val
 65                  70                  75                  80

Asp Gly Gln Leu Ile Thr Leu Glu Ser Gly Glu Phe Gln Val Tyr Lys
                 85                  90                  95

Gln Ser His Ser Ala Leu Thr Ala Leu Gln Thr Glu Gln Val Gln Asp
             100                 105                 110

Ser Glu His Ser Gly Lys Met Val Ala Lys Arg Gln Phe Arg Ile Gly
             115                 120                 125

Asp Ile Val Gly Glu His Thr Ser Phe Asp Lys Leu Pro Lys Asp Val
         130                 135                 140

Met Ala Thr Tyr Arg Gly Thr Ala Phe Gly Ser Asp Asp Ala Gly Gly
145                 150                 155                 160

Lys Leu Thr Tyr Thr Ile Asp Ala Ala Lys Gln Gly His Gly Lys Ile
                 165                 170                 175

Glu His Leu Lys Ser Pro Glu Leu Asn Val Asp Leu Ala Ala Ala Asp
             180                 185                 190

Ile Lys Pro Asp Glu Lys His His Ala Val Ile Ser Gly Ser Val Leu
         195                 200                 205

Tyr Asn Gln Ala Glu Lys Gly Ser Tyr Ser Leu Gly Ile Phe Gly Gly
    210                 215                 220

Gln Ala Gln Glu Val Ala Gly Ser Ala Glu Val Glu Thr Ala Asn Gly
225                 230                 235                 240

Ile Arg His Ile Gly Leu Ala Ala Lys Gln
                 245                 250

<210> SEQ ID NO 6
<211> LENGTH: 250
<212> TYPE: PRT
<213> ORGANISM: Neisseria meningitidis

<400> SEQUENCE: 6

Val Ala Ala Asp Ile Gly Thr Gly Leu Ala Asp Ala Leu Thr Ala Pro
 1                5                  10                  15

Leu Asp His Lys Asp Lys Gly Leu Lys Ser Leu Thr Leu Glu Asp Ser
         20                  25                  30

Ile Ser Gln Asn Gly Thr Leu Thr Leu Ser Ala Gln Gly Ala Glu Lys
         35                  40                  45

Thr Phe Lys Val Gly Asp Lys Asp Asn Ser Leu Asn Thr Gly Lys Leu
     50                  55                  60

Lys Asn Asp Lys Ile Ser Arg Phe Asp Phe Val Gln Lys Ile Glu Val
 65                  70                  75                  80

Asp Gly Gln Thr Ile Thr Leu Ala Ser Gly Glu Phe Gln Ile Tyr Lys
                 85                  90                  95

Gln Asp His Ser Ala Val Val Ala Leu Gln Ile Glu Lys Ile Asn Asn
             100                 105                 110

Pro Asp Lys Ile Asp Ser Leu Ile Asn Gln Arg Ser Phe Leu Val Ser
         115                 120                 125

Gly Leu Gly Gly Glu His Thr Ala Phe Asn Gln Leu Pro Ser Gly Lys
         130                 135                 140
```

```
Ala Glu Tyr His Gly Lys Ala Phe Ser Ser Asp Asp Ala Gly Gly Lys
145                 150                 155                 160

Leu Thr Tyr Thr Ile Asp Phe Ala Ala Lys Gln Gly His Gly Lys Ile
                165                 170                 175

Glu His Leu Lys Thr Pro Glu Gln Asn Val Glu Leu Ala Ser Ala Glu
            180                 185                 190

Leu Lys Ala Asp Glu Lys Ser His Ala Val Ile Leu Gly Asp Thr Arg
        195                 200                 205

Tyr Gly Ser Glu Glu Lys Gly Thr Tyr His Leu Ala Leu Phe Gly Asp
    210                 215                 220

Arg Ala Gln Glu Ile Ala Gly Ser Ala Thr Val Lys Ile Arg Glu Lys
225                 230                 235                 240

Val His Glu Ile Gly Ile Ala Gly Lys Gln
                245                 250

<210> SEQ ID NO 7
<211> LENGTH: 792
<212> TYPE: PRT
<213> ORGANISM: Neisseria meningitidis

<400> SEQUENCE: 7

Met Lys Pro Leu Gln Met Leu Pro Ile Ala Ala Leu Val Gly Ser Ile
1               5                   10                  15

Phe Gly Asn Pro Val Leu Ala Ala Asp Glu Ala Ala Thr Glu Thr Thr
                20                  25                  30

Pro Val Lys Ala Glu Ile Lys Ala Val Arg Val Lys Gly Gln Arg Asn
            35                  40                  45

Ala Pro Ala Ala Val Glu Arg Val Asn Leu Asn Arg Ile Lys Gln Glu
        50                  55                  60

Met Ile Arg Asp Asn Lys Asp Leu Val Arg Tyr Ser Thr Asp Val Gly
65                  70                  75                  80

Leu Ser Asp Ser Gly Arg His Gln Lys Gly Phe Ala Val Arg Gly Val
                85                  90                  95

Glu Gly Asn Arg Val Gly Val Ser Ile Asp Gly Val Asn Leu Pro Asp
                100                 105                 110

Ser Glu Glu Asn Ser Leu Tyr Ala Arg Tyr Gly Asn Phe Asn Ser Ser
            115                 120                 125

Arg Leu Ser Ile Asp Pro Glu Leu Val Arg Asn Ile Glu Ile Val Lys
        130                 135                 140

Gly Ala Asp Ser Phe Asn Thr Gly Ser Gly Ala Leu Gly Gly Gly Val
145                 150                 155                 160

Asn Tyr Gln Thr Leu Gln Gly Arg Asp Leu Leu Leu Asp Asp Arg Gln
                165                 170                 175

Phe Gly Val Met Met Lys Asn Gly Tyr Ser Thr Arg Asn Arg Glu Trp
                180                 185                 190

Thr Asn Thr Leu Gly Phe Gly Val Ser Asn Asp Arg Val Asp Ala Ala
            195                 200                 205

Leu Leu Tyr Ser Gln Arg Arg Gly His Glu Thr Glu Ser Ala Gly Asn
        210                 215                 220

Arg Gly Tyr Ala Val Glu Gly Glu Gly Ser Ala Asn Ile Arg Gly
225                 230                 235                 240

Ser Ala Arg Gly Ile Pro Asp Ser Ser Lys His Lys Tyr Asn His His
                245                 250                 255

Ala Leu Gly Lys Ile Ala Tyr Gln Ile Asn Asp Asn His Arg Ile Gly
```

```
                       260                 265                 270
Ala Ser Leu Asn Gly Gln Gln Gly His Asn Tyr Thr Val Glu Glu Ser
            275                 280                 285

Tyr Asn Leu Thr Ala Ser Ser Trp Arg Glu Ala Asp Asp Val Asn Arg
            290                 295                 300

Arg Arg Asn Ala Asn Leu Phe Tyr Glu Trp Met Pro Asp Ser Asn Trp
305                 310                 315                 320

Leu Ser Ser Leu Lys Ala Asp Phe Asp Tyr Gln Lys Thr Lys Val Ala
                325                 330                 335

Ala Val Asn Asn Lys Gly Ser Phe Pro Met Asp Tyr Ser Thr Trp Thr
            340                 345                 350

Arg Asn Tyr Asn Gln Lys Asp Leu Asp Glu Ile Tyr Asn Arg Ser Met
            355                 360                 365

Asp Thr Arg Phe Lys Arg Phe Thr Leu Arg Leu Asp Ser His Pro Leu
            370                 375                 380

Gln Leu Gly Gly Gly Arg His Arg Leu Ser Phe Lys Thr Phe Val Ser
385                 390                 395                 400

Arg Arg Asp Phe Glu Asn Leu Asn Arg Asp Asp Tyr Tyr Phe Ser Gly
                405                 410                 415

Arg Val Val Arg Thr Thr Ser Ser Ile Gln His Pro Val Lys Thr Thr
            420                 425                 430

Asn Tyr Gly Phe Ser Leu Ser Asp Gln Ile Gln Trp Asn Asp Val Phe
            435                 440                 445

Ser Ser Arg Ala Gly Ile Arg Tyr Asp His Thr Lys Met Thr Pro Gln
450                 455                 460

Glu Leu Asn Ala Glu Cys His Ala Cys Asp Lys Thr Pro Pro Ala Ala
465                 470                 475                 480

Asn Thr Tyr Lys Gly Trp Ser Gly Phe Val Gly Leu Ala Ala Gln Leu
                485                 490                 495

Asn Gln Ala Trp Arg Val Gly Tyr Asp Ile Thr Ser Gly Tyr Arg Val
            500                 505                 510

Pro Asn Ala Ser Glu Val Tyr Phe Thr Tyr Asn His Gly Ser Gly Asn
            515                 520                 525

Trp Leu Pro Asn Pro Asn Leu Lys Ala Glu Arg Ser Thr Thr His Thr
            530                 535                 540

Leu Ser Leu Gln Gly Arg Ser Glu Lys Gly Met Leu Asp Ala Asn Leu
545                 550                 555                 560

Tyr Gln Ser Asn Tyr Arg Asn Phe Leu Ser Glu Glu Gln Lys Leu Thr
                565                 570                 575

Thr Ser Gly Thr Pro Gly Cys Thr Glu Glu Asn Ala Tyr Tyr Gly Ile
            580                 585                 590

Cys Ser Asp Pro Tyr Lys Glu Lys Leu Asp Trp Gln Met Lys Asn Ile
            595                 600                 605

Asp Lys Ala Arg Ile Arg Gly Ile Glu Leu Thr Gly Arg Leu Asn Val
            610                 615                 620

Asp Lys Val Ala Ser Phe Val Pro Glu Gly Trp Lys Leu Phe Gly Ser
625                 630                 635                 640

Leu Gly Tyr Ala Lys Ser Lys Leu Ser Gly Asp Asn Ser Leu Leu Ser
                645                 650                 655

Thr Gln Pro Leu Lys Val Ile Ala Gly Ile Asp Tyr Glu Ser Pro Ser
            660                 665                 670

Glu Lys Trp Gly Val Phe Ser Arg Leu Thr Tyr Leu Gly Ala Lys Lys
            675                 680                 685
```

```
Val Lys Asp Ala Gln Tyr Thr Val Tyr Glu Asn Lys Gly Trp Gly Thr
            690                 695                 700

Pro Leu Gln Lys Lys Val Lys Asp Tyr Pro Trp Leu Asn Lys Ser Ala
705                 710                 715                 720

Tyr Val Phe Asp Met Tyr Gly Phe Tyr Lys Pro Ala Lys Asn Leu Thr
                725                 730                 735

Leu Arg Ala Gly Val Tyr Asn Leu Phe Asn Arg Lys Tyr Thr Thr Trp
            740                 745                 750

Asp Ser Leu Arg Gly Leu Tyr Ser Tyr Ser Thr Thr Asn Ala Val Asp
        755                 760                 765

Arg Asp Gly Lys Gly Leu Asp Arg Tyr Arg Ala Pro Gly Arg Asn Tyr
    770                 775                 780

Ala Val Ser Leu Glu Trp Lys Phe
785                 790

<210> SEQ ID NO 8
<211> LENGTH: 793
<212> TYPE: PRT
<213> ORGANISM: Neisseria meningitidis

<400> SEQUENCE: 8

Met Lys Pro Leu Gln Met Leu Pro Ile Ala Ala Leu Val Gly Ser Ile
1               5                   10                  15

Phe Gly Asn Pro Val Phe Ala Ala Asp Glu Ala Ala Thr Glu Thr Thr
            20                  25                  30

Pro Val Lys Ala Glu Val Lys Ala Val Arg Val Lys Gly Gln Arg Asn
        35                  40                  45

Ala Pro Ala Ala Val Glu Arg Val Asn Leu Asn Arg Ile Lys Gln Glu
    50                  55                  60

Met Ile Arg Asp Asn Lys Asp Leu Val Arg Tyr Ser Thr Asp Val Gly
65                  70                  75                  80

Leu Ser Asp Ser Gly Arg His Gln Lys Gly Phe Ala Val Arg Gly Val
                85                  90                  95

Glu Gly Asn Arg Val Gly Val Ser Ile Asp Gly Val Asn Leu Pro Asp
            100                 105                 110

Ser Glu Glu Asn Ser Leu Tyr Ala Arg Tyr Gly Asn Phe Asn Ser Ser
        115                 120                 125

Arg Leu Ser Ile Asp Pro Glu Leu Val Arg Asn Ile Asp Ile Val Lys
    130                 135                 140

Gly Ala Asp Ser Phe Asn Thr Gly Ser Gly Ala Leu Gly Gly Gly Val
145                 150                 155                 160

Asn Tyr Gln Thr Leu Gln Gly Arg Asp Leu Leu Pro Glu Arg Gln
                165                 170                 175

Phe Gly Val Met Met Lys Asn Gly Tyr Ser Thr Arg Asn Arg Glu Trp
            180                 185                 190

Thr Asn Thr Leu Gly Phe Gly Val Ser Asn Asp Arg Val Asp Ala Ala
        195                 200                 205

Leu Leu Tyr Ser Gln Arg Arg Gly His Glu Thr Glu Ser Ala Gly Lys
    210                 215                 220

Arg Gly Tyr Pro Val Glu Gly Ala Gly Ser Gly Ala Asn Ile Arg Gly
225                 230                 235                 240

Ser Ala Arg Gly Ile Pro Asp Pro Ser Gln His Lys Tyr Asn His His
                245                 250                 255

Ala Leu Gly Lys Ile Ala Tyr Gln Ile Asn Asp Asn His Arg Ile Gly
```

```
                    260                 265                 270
Ala Ser Leu Asn Gly Gln Gln Gly His Asn Tyr Thr Val Glu Glu Ser
            275                 280                 285

Tyr Asn Leu Leu Ala Ser Tyr Trp Arg Glu Ala Asp Val Asn Arg
    290                 295                 300

Arg Arg Asn Thr Asn Leu Phe Tyr Glu Trp Thr Pro Glu Ser Asp Arg
305                 310                 315                 320

Leu Ser Met Val Lys Ala Asp Val Asp Tyr Gln Lys Thr Lys Val Ser
                325                 330                 335

Ala Val Asn Tyr Lys Gly Ser Phe Pro Ile Glu Asp Ser Ser Thr Leu
            340                 345                 350

Thr Arg Asn Tyr Asn Gln Lys Asp Leu Asp Glu Ile Tyr Asn Arg Ser
        355                 360                 365

Met Asp Thr Arg Phe Lys Arg Ile Thr Leu Arg Leu Asp Ser His Pro
    370                 375                 380

Leu Gln Leu Gly Gly Gly Arg His Arg Leu Ser Phe Lys Thr Phe Ala
385                 390                 395                 400

Ser Arg Arg Asp Phe Glu Asn Leu Asn Arg Asp Asp Tyr Tyr Phe Ser
                405                 410                 415

Gly Arg Val Val Arg Thr Thr Ser Ser Ile Gln His Pro Val Lys Thr
            420                 425                 430

Thr Asn Tyr Gly Phe Ser Leu Ser Asp Gln Ile Gln Trp Asn Asp Val
        435                 440                 445

Phe Ser Ser Arg Ala Gly Ile Arg Tyr Asp His Thr Lys Met Thr Pro
    450                 455                 460

Gln Glu Leu Asn Ala Glu Cys His Ala Cys Asp Lys Thr Pro Pro Ala
465                 470                 475                 480

Ala Asn Thr Tyr Lys Gly Trp Ser Gly Phe Val Gly Leu Ala Ala Gln
                485                 490                 495

Leu Asn Gln Ala Trp Arg Val Gly Tyr Asp Ile Thr Ser Gly Tyr Arg
            500                 505                 510

Val Pro Asn Ala Ser Glu Val Tyr Phe Thr Tyr Asn His Gly Ser Gly
        515                 520                 525

Asn Trp Leu Pro Asn Pro Asn Leu Lys Ala Glu Arg Thr Thr Thr His
    530                 535                 540

Thr Leu Ser Leu Gln Gly Arg Ser Glu Lys Gly Thr Leu Asp Ala Asn
545                 550                 555                 560

Leu Tyr Gln Ser Asn Tyr Arg Asn Phe Leu Ser Glu Glu Gln Lys Leu
                565                 570                 575

Thr Thr Ser Gly Asp Val Ser Cys Thr Gln Met Asn Tyr Tyr Tyr Gly
            580                 585                 590

Met Cys Ser Asn Pro Tyr Ser Glu Lys Leu Glu Trp Gln Met Gln Asn
        595                 600                 605

Ile Asp Lys Ala Arg Ile Arg Gly Ile Glu Leu Thr Gly Arg Leu Asn
    610                 615                 620

Val Asp Lys Val Ala Ser Phe Val Pro Glu Gly Trp Lys Leu Phe Gly
625                 630                 635                 640

Ser Leu Gly Tyr Ala Lys Ser Lys Leu Ser Gly Asp Asn Ser Leu Leu
                645                 650                 655

Ser Thr Gln Pro Leu Lys Val Ile Ala Gly Ile Asp Tyr Glu Ser Pro
            660                 665                 670

Ser Glu Lys Trp Gly Val Phe Ser Arg Leu Thr Tyr Leu Gly Ala Lys
        675                 680                 685
```

```
Lys Val Lys Asp Ala Gln Tyr Thr Val Tyr Glu Asn Lys Gly Trp Gly
            690                 695                 700

Thr Pro Leu Gln Lys Lys Val Lys Asp Tyr Pro Trp Leu Asn Lys Ser
705                 710                 715                 720

Ala Tyr Val Phe Asp Met Tyr Gly Phe Tyr Lys Pro Val Lys Asn Leu
                725                 730                 735

Thr Leu Arg Ala Gly Val Tyr Asn Val Phe Asn Arg Lys Tyr Thr Thr
            740                 745                 750

Trp Asp Ser Leu Arg Gly Leu Tyr Ser Tyr Ser Thr Thr Asn Ser Val
        755                 760                 765

Asp Arg Asp Gly Lys Gly Leu Asp Arg Tyr Arg Ala Pro Ser Arg Asn
    770                 775                 780

Tyr Ala Val Ser Leu Glu Trp Lys Phe
785                 790

<210> SEQ ID NO 9
<211> LENGTH: 488
<212> TYPE: PRT
<213> ORGANISM: Neisseria meningitidis

<400> SEQUENCE: 9

Met Phe Lys Arg Ser Val Ile Ala Met Ala Cys Ile Phe Ala Leu Ser
1               5                   10                  15

Ala Cys Gly Gly Gly Gly Gly Ser Pro Asp Val Lys Ser Ala Asp
            20                  25                  30

Thr Leu Ser Lys Pro Ala Ala Pro Val Val Ser Glu Lys Glu Thr Glu
        35                  40                  45

Ala Lys Glu Asp Ala Pro Gln Ala Gly Ser Gln Gly Gln Gly Ala Pro
    50                  55                  60

Ser Ala Gln Gly Ser Gln Asp Met Ala Ala Val Ser Glu Glu Asn Thr
65                  70                  75                  80

Gly Asn Gly Gly Ala Val Thr Ala Asp Asn Pro Lys Asn Glu Asp Glu
                85                  90                  95

Val Ala Gln Asn Asp Met Pro Gln Asn Ala Ala Gly Thr Asp Ser Ser
            100                 105                 110

Thr Pro Asn His Thr Pro Asp Pro Asn Met Leu Ala Gly Asn Met Glu
        115                 120                 125

Asn Gln Ala Thr Asp Ala Gly Glu Ser Ser Gln Pro Ala Asn Gln Pro
    130                 135                 140

Asp Met Ala Asn Ala Ala Asp Gly Met Gln Gly Asp Asp Pro Ser Ala
145                 150                 155                 160

Gly Gly Gln Asn Ala Gly Asn Thr Ala Ala Gln Gly Ala Asn Gln Ala
                165                 170                 175

Gly Asn Asn Gln Ala Ala Gly Ser Ser Asp Pro Ile Pro Ala Ser Asn
            180                 185                 190

Pro Ala Pro Ala Asn Gly Gly Ser Asn Phe Gly Arg Val Asp Leu Ala
        195                 200                 205

Asn Gly Val Leu Ile Asp Gly Pro Ser Gln Asn Ile Thr Leu Thr His
    210                 215                 220

Cys Lys Gly Asp Ser Cys Ser Gly Asn Asn Phe Leu Asp Glu Val
225                 230                 235                 240

Gln Leu Lys Ser Glu Phe Glu Lys Leu Ser Asp Ala Asp Lys Ile Ser
                245                 250                 255

Asn Tyr Lys Lys Asp Gly Lys Asn Asp Lys Phe Val Gly Leu Val Ala
```

-continued

```
                260                 265                 270
Asp Ser Val Gln Met Lys Gly Ile Asn Gln Tyr Ile Ile Phe Tyr Lys
        275                 280                 285

Pro Lys Pro Thr Ser Phe Ala Arg Phe Arg Arg Ser Ala Arg Ser Arg
        290                 295                 300

Arg Ser Leu Pro Ala Glu Met Pro Leu Ile Pro Val Asn Gln Ala Asp
305                 310                 315                 320

Thr Leu Ile Val Asp Gly Glu Ala Val Ser Leu Thr Gly His Ser Gly
                325                 330                 335

Asn Ile Phe Ala Pro Glu Gly Asn Tyr Arg Tyr Leu Thr Tyr Gly Ala
                340                 345                 350

Glu Lys Leu Pro Gly Gly Ser Tyr Ala Leu Arg Val Gln Gly Glu Pro
        355                 360                 365

Ala Lys Gly Glu Met Leu Ala Gly Ala Val Tyr Asn Gly Glu Val
        370                 375                 380

Leu His Phe His Thr Glu Asn Gly Arg Pro Tyr Pro Thr Arg Gly Arg
385                 390                 395                 400

Phe Ala Ala Lys Val Asp Phe Gly Ser Lys Ser Val Asp Gly Ile Ile
                405                 410                 415

Asp Ser Gly Asp Asp Leu His Met Gly Thr Gln Lys Phe Lys Ala Ala
                420                 425                 430

Ile Asp Gly Asn Gly Phe Lys Gly Thr Trp Thr Glu Asn Gly Ser Gly
                435                 440                 445

Asp Val Ser Gly Lys Phe Tyr Gly Pro Ala Gly Glu Glu Val Ala Gly
        450                 455                 460

Lys Tyr Ser Tyr Arg Pro Thr Asp Ala Glu Lys Gly Gly Phe Gly Val
465                 470                 475                 480

Phe Ala Gly Lys Lys Glu Gln Asp
                485

<210> SEQ ID NO 10
<211> LENGTH: 364
<212> TYPE: PRT
<213> ORGANISM: Neisseria meningitidis

<400> SEQUENCE: 10

Met Ser Met Lys His Phe Pro Ser Lys Val Leu Thr Thr Ala Ile Leu
1               5                   10                  15

Ala Thr Phe Cys Ser Gly Ala Leu Ala Ala Thr Ser Asp Asp Asp Val
                20                  25                  30

Lys Lys Ala Ala Thr Val Ala Ile Val Ala Ala Tyr Asn Asn Gly Gln
            35                  40                  45

Glu Ile Asn Gly Phe Lys Ala Gly Glu Thr Ile Tyr Asp Ile Gly Glu
        50                  55                  60

Asp Gly Thr Ile Thr Gln Lys Asp Ala Thr Ala Asp Val Glu Ala
65                  70                  75                  80

Asp Asp Phe Lys Gly Leu Gly Leu Lys Lys Val Val Thr Asn Leu Thr
                85                  90                  95

Lys Thr Val Asn Glu Asn Lys Gln Asn Val Asp Ala Lys Val Lys Ala
                100                 105                 110

Ala Glu Ser Glu Ile Glu Lys Leu Thr Thr Lys Leu Ala Asp Thr Asp
        115                 120                 125

Ala Ala Leu Ala Asp Thr Asp Ala Ala Leu Asp Glu Thr Thr Asn Ala
    130                 135                 140
```

```
Leu Asn Lys Leu Gly Glu Asn Ile Thr Thr Phe Ala Glu Glu Thr Lys
145                 150                 155                 160

Thr Asn Ile Val Lys Ile Asp Glu Lys Leu Glu Ala Val Ala Asp Thr
            165                 170                 175

Val Asp Lys His Ala Glu Ala Phe Asn Asp Ile Ala Asp Ser Leu Asp
            180                 185                 190

Glu Thr Asn Thr Lys Ala Asp Glu Ala Val Lys Thr Ala Asn Glu Ala
        195                 200                 205

Lys Gln Thr Ala Glu Glu Thr Lys Gln Asn Val Asp Ala Lys Val Lys
    210                 215                 220

Ala Ala Glu Thr Ala Ala Gly Lys Ala Glu Ala Ala Gly Thr Ala
225                 230                 235                 240

Asn Thr Ala Ala Asp Lys Ala Glu Ala Val Ala Lys Val Thr Asp
            245                 250                 255

Ile Lys Ala Asp Ile Ala Thr Asn Lys Ala Asp Ile Ala Lys Asn Ser
            260                 265                 270

Ala Arg Ile Asp Ser Leu Asp Lys Asn Val Ala Asn Leu Arg Lys Glu
        275                 280                 285

Thr Arg Gln Gly Leu Ala Glu Gln Ala Ala Leu Ser Gly Leu Phe Gln
    290                 295                 300

Pro Tyr Asn Val Gly Arg Phe Asn Val Thr Ala Ala Val Gly Tyr
305                 310                 315                 320

Lys Ser Glu Ser Ala Val Ala Ile Gly Thr Gly Phe Arg Phe Thr Glu
            325                 330                 335

Asn Phe Ala Ala Lys Ala Gly Val Ala Val Gly Thr Ser Ser Gly Ser
        340                 345                 350

Ser Ala Ala Tyr His Val Gly Val Asn Tyr Glu Trp
        355                 360

<210> SEQ ID NO 11
<211> LENGTH: 174
<212> TYPE: PRT
<213> ORGANISM: Neisseria meningitidis

<400> SEQUENCE: 11

Met Lys Lys Ala Leu Ala Thr Leu Ile Ala Leu Ala Leu Pro Ala Ala
1               5                   10                  15

Ala Leu Ala Glu Gly Ala Ser Gly Phe Tyr Val Gln Ala Asp Ala Ala
            20                  25                  30

His Ala Lys Ala Ser Ser Ser Leu Gly Ser Ala Lys Gly Phe Ser Pro
        35                  40                  45

Arg Ile Ser Ala Gly Tyr Arg Ile Asn Asp Leu Arg Phe Ala Val Asp
    50                  55                  60

Tyr Thr Arg Tyr Lys Asn Tyr Lys Ala Pro Ser Thr Asp Phe Lys Leu
65                  70                  75                  80

Tyr Ser Ile Gly Ala Ser Ala Ile Tyr Asp Phe Asp Thr Gln Ser Pro
                85                  90                  95

Val Lys Pro Tyr Leu Gly Ala Arg Leu Ser Leu Asn Arg Ala Ser Val
            100                 105                 110

Asp Leu Gly Gly Ser Asp Ser Phe Ser Gln Thr Ser Ile Gly Leu Gly
        115                 120                 125

Val Leu Thr Gly Val Ser Tyr Ala Val Thr Pro Asn Val Asp Leu Asp
    130                 135                 140

Ala Gly Tyr Arg Tyr Asn Tyr Ile Gly Lys Val Asn Thr Val Lys Asn
145                 150                 155                 160
```

```
Val Arg Ser Gly Glu Leu Ser Ala Gly Val Arg Val Lys Phe
            165                 170

<210> SEQ ID NO 12
<211> LENGTH: 591
<212> TYPE: PRT
<213> ORGANISM: Neisseria meningitidis

<400> SEQUENCE: 12

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
            20                  25                  30

Thr Val Lys Thr Ala Val Leu Ala Thr Leu Leu Phe Ala Thr Val Gln
        35                  40                  45

Ala Ser Ala Asn Asn Glu Glu Gln Glu Glu Asp Leu Tyr Leu Asp Pro
    50                  55                  60

Val Gln Arg Thr Val Ala Val Leu Ile Val Asn Ser Asp Lys Glu Gly
65                  70                  75                  80

Thr Gly Glu Lys Glu Lys Val Glu Glu Asn Ser Asp Trp Ala Val Tyr
                85                  90                  95

Phe Asn Glu Lys Gly Val Leu Thr Ala Arg Glu Ile Thr Leu Lys Ala
            100                 105                 110

Gly Asp Asn Leu Lys Ile Lys Gln Asn Gly Thr Asn Phe Thr Tyr Ser
        115                 120                 125

Leu Lys Lys Asp Leu Thr Asp Leu Thr Ser Val Gly Thr Glu Lys Leu
130                 135                 140

Ser Phe Ser Ala Asn Gly Asn Lys Val Asn Ile Thr Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Thr Leu Leu Asn
            180                 185                 190

Thr Gly Ala Thr Thr Asn Val Thr Asn Asp Asn Val Thr Asp Asp Glu
        195                 200                 205

Lys Lys Arg Ala Ala Ser Val Lys Asp Val Leu Asn Ala Gly Trp Asn
    210                 215                 220

Ile Lys Gly Val Lys Pro Gly Thr Thr Ala Ser Asp Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Lys Thr Glu Val
            260                 265                 270

Lys Ile Gly Ala Lys Thr Ser Val Ile Lys Glu Lys Asp Gly Lys Leu
        275                 280                 285

Val Thr Gly Lys Asp Lys Gly Glu Asn Gly Ser Ser Thr Asp Glu Gly
    290                 295                 300

Glu Gly Leu Val Thr Ala Lys Glu Val Ile Asp Ala Val Asn Lys Ala
305                 310                 315                 320

Gly Trp Arg Met Lys Thr Thr Thr Ala Asn Gly Gln Thr Gly Gln Ala
                325                 330                 335

Asp Lys Phe Glu Thr Val Thr Ser Gly Thr Asn Val Thr Phe Ala Ser
            340                 345                 350

Gly Lys Gly Thr Thr Ala Thr Val Ser Lys Asp Asp Gln Gly Asn Ile
```

```
                    355                 360                 365
Thr Val Met Tyr Asp Val Asn Val Gly Asp Ala Leu Asn Val Asn Gln
370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
                    405                 410                 415

Asp Glu Thr Val Asn Ile Asn Ala Gly Asn Asn Ile Glu Ile Thr Arg
                420                 425                 430

Asn Gly Lys Asn Ile Asp Ile Ala Thr Ser Met Thr Pro Gln Phe Ser
            435                 440                 445

Ser Val Ser Leu Gly Ala Gly Ala Asp Ala Pro Thr Leu Ser Val Asp
        450                 455                 460

Gly Asp Ala Leu Asn Val Gly Ser Lys Lys Asp Asn Lys Pro Val Arg
465                 470                 475                 480

Ile Thr Asn Val Ala Pro Gly Val Lys Glu Gly Asp Val Thr Asn Val
                    485                 490                 495

Ala Gln Leu Lys Gly Val Ala Gln Asn Leu Asn Asn Arg Ile Asp Asn
                500                 505                 510

Val Asp Gly Asn Ala Arg Ala Gly Ile Ala Gln Ala Ile Ala Thr Ala
            515                 520                 525

Gly Leu Val Gln Ala Tyr Leu Pro Gly Lys Ser Met Met Ala Ile Gly
        530                 535                 540

Gly Gly Thr Tyr Arg Gly Glu Ala Gly Tyr Ala Ile Gly Tyr Ser Ser
545                 550                 555                 560

Ile Ser Asp Gly Gly Asn Trp Ile Ile Lys Gly Thr Ala Ser Gly Asn
                    565                 570                 575

Ser Arg Gly His Phe Gly Ala Ser Ala Ser Val Gly Tyr Gln Trp
                580                 585                 590

<210> SEQ ID NO 13
<211> LENGTH: 1457
<212> TYPE: PRT
<213> ORGANISM: Neisseria meningitidis

<400> SEQUENCE: 13

Met Lys Thr Thr Asp Lys Arg Thr Thr Glu Thr His Arg Lys Ala Pro
1               5                   10                  15

Lys Thr Gly Arg Ile Arg Phe Ser Pro Ala Tyr Leu Ala Ile Cys Leu
                20                  25                  30

Ser Phe Gly Ile Leu Pro Gln Ala Trp Ala Gly His Thr Tyr Phe Gly
            35                  40                  45

Ile Asn Tyr Gln Tyr Tyr Arg Asp Phe Ala Glu Asn Lys Gly Lys Phe
        50                  55                  60

Ala Val Gly Ala Lys Asp Ile Glu Val Tyr Asn Lys Lys Gly Glu Leu
65                  70                  75                  80

Val Gly Lys Ser Met Thr Lys Ala Pro Met Ile Asp Phe Ser Val Val
                85                  90                  95

Ser Arg Asn Gly Val Ala Ala Leu Val Gly Asp Gln Tyr Ile Val Ser
                100                 105                 110

Val Ala His Asn Gly Gly Tyr Asn Asn Val Asp Phe Gly Ala Glu Gly
            115                 120                 125

Arg Asn Pro Asp Gln His Arg Phe Thr Tyr Lys Ile Val Lys Arg Asn
        130                 135                 140
```

-continued

```
Asn Tyr Lys Ala Gly Thr Lys Gly His Pro Tyr Gly Gly Asp Tyr His
145                 150                 155                 160

Met Pro Arg Leu His Lys Phe Val Thr Asp Ala Glu Pro Val Glu Met
                165                 170                 175

Thr Ser Tyr Met Asp Gly Arg Lys Tyr Ile Asp Gln Asn Asn Tyr Pro
            180                 185                 190

Asp Arg Val Arg Ile Gly Ala Gly Arg Gln Tyr Trp Arg Ser Asp Glu
        195                 200                 205

Asp Glu Pro Asn Asn Arg Glu Ser Ser Tyr His Ile Ala Ser Ala Tyr
    210                 215                 220

Ser Trp Leu Val Gly Gly Asn Thr Phe Ala Gln Asn Gly Ser Gly Gly
225                 230                 235                 240

Gly Thr Val Asn Leu Gly Ser Glu Lys Ile Lys His Ser Pro Tyr Gly
                245                 250                 255

Phe Leu Pro Thr Gly Gly Ser Phe Gly Asp Ser Gly Ser Pro Met Phe
            260                 265                 270

Ile Tyr Asp Ala Gln Lys Gln Lys Trp Leu Ile Asn Gly Val Leu Gln
        275                 280                 285

Thr Gly Asn Pro Tyr Ile Gly Lys Ser Asn Gly Phe Gln Leu Val Arg
    290                 295                 300

Lys Asp Trp Phe Tyr Asp Glu Ile Phe Ala Gly Asp Thr His Ser Val
305                 310                 315                 320

Phe Tyr Glu Pro Arg Gln Asn Gly Lys Tyr Ser Phe Asn Asp Asp Asn
                325                 330                 335

Asn Gly Thr Gly Lys Ile Asn Ala Lys His Glu His Asn Ser Leu Pro
            340                 345                 350

Asn Arg Leu Lys Thr Arg Thr Val Gln Leu Phe Asn Val Ser Leu Ser
        355                 360                 365

Glu Thr Ala Arg Glu Pro Val Tyr His Ala Ala Gly Gly Val Asn Ser
    370                 375                 380

Tyr Arg Pro Arg Leu Asn Asn Gly Glu Asn Ile Ser Phe Ile Asp Glu
385                 390                 395                 400

Gly Lys Gly Glu Leu Ile Leu Thr Ser Asn Ile Asn Gln Gly Ala Gly
                405                 410                 415

Gly Leu Tyr Phe Gln Gly Asp Phe Thr Val Ser Pro Glu Asn Asn Glu
            420                 425                 430

Thr Trp Gln Gly Ala Gly Val His Ile Ser Glu Asp Ser Thr Val Thr
        435                 440                 445

Trp Lys Val Asn Gly Val Ala Asn Asp Arg Leu Ser Lys Ile Gly Lys
    450                 455                 460

Gly Thr Leu His Val Gln Ala Lys Gly Glu Asn Gln Gly Ser Ile Ser
465                 470                 475                 480

Val Gly Asp Gly Thr Val Ile Leu Asp Gln Gln Ala Asp Asp Lys Gly
                485                 490                 495

Lys Lys Gln Ala Phe Ser Glu Ile Gly Leu Val Ser Gly Arg Gly Thr
            500                 505                 510

Val Gln Leu Asn Ala Asp Asn Gln Phe Asn Pro Asp Lys Leu Tyr Phe
        515                 520                 525

Gly Phe Arg Gly Gly Arg Leu Asp Leu Asn Gly His Ser Leu Ser Phe
    530                 535                 540

His Arg Ile Gln Asn Thr Asp Glu Gly Ala Met Ile Val Asn His Asn
545                 550                 555                 560

Gln Asp Lys Glu Ser Thr Val Thr Ile Thr Gly Asn Lys Asp Ile Ala
```

```
                565                 570                 575
Thr Thr Gly Asn Asn Asn Ser Leu Asp Ser Lys Lys Glu Ile Ala Tyr
            580                 585                 590

Asn Gly Trp Phe Gly Glu Lys Asp Thr Thr Lys Thr Asn Gly Arg Leu
            595                 600             605

Asn Leu Val Tyr Gln Pro Ala Glu Asp Arg Thr Leu Leu Leu Ser
        610                 615             620

Gly Gly Thr Asn Leu Asn Gly Asn Ile Thr Gln Thr Asn Gly Lys Leu
625             630                 635                 640

Phe Phe Ser Gly Arg Pro Thr Pro His Ala Tyr Asn His Leu Asn Asp
                645             650                 655

His Trp Ser Gln Lys Glu Gly Ile Pro Arg Gly Glu Ile Val Trp Asp
            660                 665             670

Asn Asp Trp Ile Asn Arg Thr Phe Lys Ala Glu Asn Phe Gln Ile Lys
        675                 680             685

Gly Gly Gln Ala Val Val Ser Arg Asn Val Ala Lys Val Lys Gly Asp
        690                 695             700

Trp His Leu Ser Asn His Ala Gln Ala Val Phe Gly Val Ala Pro His
705             710                 715                 720

Gln Ser His Thr Ile Cys Thr Arg Ser Asp Trp Thr Gly Leu Thr Asn
                725                 730                 735

Cys Val Glu Lys Thr Ile Thr Asp Asp Lys Val Ile Ala Ser Leu Thr
            740                 745             750

Lys Thr Asp Ile Ser Gly Asn Val Asp Leu Ala Asp His Ala His Leu
            755                 760                 765

Asn Leu Thr Gly Leu Ala Thr Leu Asn Gly Asn Leu Ser Ala Asn Gly
        770                 775                 780

Asp Thr Arg Tyr Thr Val Ser His Asn Ala Thr Gln Asn Gly Asn Leu
785             790                 795                 800

Ser Leu Val Gly Asn Ala Gln Ala Thr Phe Asn Gln Ala Thr Leu Asn
                805                 810                 815

Gly Asn Thr Ser Ala Ser Gly Asn Ala Ser Phe Asn Leu Ser Asp His
            820                 825                 830

Ala Val Gln Asn Gly Ser Leu Thr Leu Ser Gly Asn Ala Lys Ala Asn
            835                 840                 845

Val Ser His Ser Ala Leu Asn Gly Asn Val Ser Leu Ala Asp Lys Ala
850                 855                 860

Val Phe His Phe Glu Ser Ser Arg Phe Thr Gly Gln Ile Ser Gly Gly
865                 870                 875                 880

Lys Asp Thr Ala Leu His Leu Lys Asp Ser Glu Trp Thr Leu Pro Ser
                885                 890                 895

Gly Thr Glu Leu Gly Asn Leu Asn Leu Asp Asn Ala Thr Ile Thr Leu
            900                 905                 910

Asn Ser Ala Tyr Arg His Asp Ala Ala Gly Ala Gln Thr Gly Ser Ala
            915                 920                 925

Thr Asp Ala Pro Arg Arg Ser Arg Ser Arg Ser Arg Ser Leu Leu
930                 935                 940

Ser Val Thr Pro Pro Thr Ser Val Glu Ser Arg Phe Asn Thr Leu Thr
945                 950                 955                 960

Val Asn Gly Lys Leu Asn Gly Gln Gly Thr Phe Arg Phe Met Ser Glu
            965                 970                 975

Leu Phe Gly Tyr Arg Ser Asp Lys Leu Lys Leu Ala Glu Ser Ser Glu
            980                 985                 990
```

```
Gly Thr Tyr Thr Leu Ala Val Asn Asn Thr Gly Asn Glu Pro Ala Ser
        995                 1000                1005

Leu Glu Gln Leu Thr Val Val Glu Gly Lys Asp Asn Lys Pro Leu Ser
    1010                1015                1020

Glu Asn Leu Asn Phe Thr Leu Gln Asn Glu His Val Asp Ala Gly Ala
1025                1030                1035                1040

Trp Arg Tyr Gln Leu Ile Arg Lys Asp Gly Glu Phe Arg Leu His Asn
        1045                1050                1055

Pro Val Lys Glu Gln Glu Leu Ser Asp Lys Leu Gly Lys Ala Glu Ala
            1060                1065                1070

Lys Lys Gln Ala Glu Lys Asp Asn Ala Gln Ser Leu Asp Ala Leu Ile
        1075                1080                1085

Ala Ala Gly Arg Asp Ala Val Glu Lys Thr Glu Ser Val Ala Glu Pro
    1090                1095                1100

Ala Arg Gln Ala Gly Gly Glu Asn Val Gly Ile Met Gln Ala Glu Glu
1105                1110                1115                1120

Glu Lys Lys Arg Val Gln Ala Asp Lys Asp Thr Ala Leu Ala Lys Gln
        1125                1130                1135

Arg Glu Ala Glu Thr Arg Pro Ala Thr Thr Ala Phe Pro Arg Ala Arg
        1140                1145                1150

Arg Ala Arg Arg Asp Leu Pro Gln Leu Gln Pro Gln Pro Gln Pro Gln
    1155                1160                1165

Pro Gln Arg Asp Leu Ile Ser Arg Tyr Ala Asn Ser Gly Leu Ser Glu
    1170                1175                1180

Phe Ser Ala Thr Leu Asn Ser Val Phe Ala Val Gln Asp Glu Leu Asp
1185                1190                1195                1200

Arg Val Phe Ala Glu Asp Arg Arg Asn Ala Val Trp Thr Ser Gly Ile
        1205                1210                1215

Arg Asp Thr Lys His Tyr Arg Ser Gln Asp Phe Arg Ala Tyr Arg Gln
        1220                1225                1230

Gln Thr Asp Leu Arg Gln Ile Gly Met Gln Lys Asn Leu Gly Ser Gly
        1235                1240                1245

Arg Val Gly Ile Leu Phe Ser His Asn Arg Thr Glu Asn Thr Phe Asp
    1250                1255                1260

Asp Gly Ile Gly Asn Ser Ala Arg Leu Ala His Gly Ala Val Phe Gly
1265                1270                1275                1280

Gln Tyr Gly Ile Asp Arg Phe Tyr Ile Gly Ile Ser Ala Gly Ala Gly
        1285                1290                1295

Phe Ser Ser Gly Ser Leu Ser Asp Gly Ile Gly Lys Ile Arg Arg
            1300                1305                1310

Arg Val Leu His Tyr Gly Ile Gln Ala Arg Tyr Arg Ala Gly Phe Gly
        1315                1320                1325

Gly Phe Gly Ile Glu Pro His Ile Gly Ala Thr Arg Tyr Phe Val Gln
    1330                1335                1340

Lys Ala Asp Tyr Arg Tyr Glu Asn Val Asn Ile Ala Thr Pro Gly Leu
1345                1350                1355                1360

Ala Phe Asn Arg Tyr Arg Ala Gly Ile Lys Ala Asp Tyr Ser Phe Lys
        1365                1370                1375

Pro Ala Gln His Ile Ser Ile Thr Pro Tyr Leu Ser Leu Ser Tyr Thr
            1380                1385                1390

Asp Ala Ala Ser Gly Lys Val Arg Thr Arg Val Asn Thr Ala Val Leu
        1395                1400                1405
```

```
Ala Gln Asp Phe Gly Lys Thr Arg Ser Ala Glu Trp Gly Val Asn Ala
    1410                1415                1420

Glu Ile Lys Gly Phe Thr Leu Ser Leu His Ala Ala Ala Lys Gly
1425                1430                1435                1440

Pro Gln Leu Glu Ala Gln His Ser Ala Gly Ile Lys Leu Gly Tyr Arg
                1445                1450                1455

Trp

<210> SEQ ID NO 14
<211> LENGTH: 797
<212> TYPE: PRT
<213> ORGANISM: Neisseria meningitidis

<400> SEQUENCE: 14

Met Lys Leu Lys Gln Ile Ala Ser Ala Leu Met Met Leu Gly Ile Ser
1               5                   10                  15

Pro Leu Ala Leu Ala Asp Phe Thr Ile Gln Asp Ile Arg Val Glu Gly
            20                  25                  30

Leu Gln Arg Thr Glu Pro Ser Thr Val Phe Asn Tyr Leu Pro Val Lys
        35                  40                  45

Val Gly Asp Thr Tyr Asn Asp Thr His Gly Ser Ala Ile Ile Lys Ser
50                  55                  60

Leu Tyr Ala Thr Gly Phe Phe Asp Asp Val Arg Val Glu Thr Ala Asp
65                  70                  75                  80

Gly Gln Leu Leu Leu Thr Val Ile Glu Arg Pro Thr Ile Gly Ser Leu
                85                  90                  95

Asn Ile Thr Gly Ala Lys Met Leu Gln Asn Asp Ala Ile Lys Lys Asn
            100                 105                 110

Leu Glu Ser Phe Gly Leu Ala Gln Ser Gln Tyr Phe Asn Gln Ala Thr
        115                 120                 125

Leu Asn Gln Ala Val Ala Gly Leu Lys Glu Glu Tyr Leu Gly Arg Gly
130                 135                 140

Lys Leu Asn Ile Gln Ile Thr Pro Lys Val Thr Lys Leu Ala Arg Asn
145                 150                 155                 160

Arg Val Asp Ile Asp Ile Thr Ile Asp Glu Gly Lys Ser Ala Lys Ile
                165                 170                 175

Thr Asp Ile Glu Phe Glu Gly Asn Gln Val Tyr Ser Asp Arg Lys Leu
            180                 185                 190

Met Arg Gln Met Ser Leu Thr Glu Gly Gly Ile Trp Thr Trp Leu Thr
        195                 200                 205

Arg Ser Asn Gln Phe Asn Glu Gln Lys Phe Ala Gln Asp Met Glu Lys
210                 215                 220

Val Thr Asp Phe Tyr Gln Asn Asn Gly Tyr Phe Asp Phe Arg Ile Leu
225                 230                 235                 240

Asp Thr Asp Ile Gln Thr Asn Glu Asp Lys Thr Lys Gln Thr Ile Lys
                245                 250                 255

Ile Thr Val His Glu Gly Gly Arg Phe Arg Trp Gly Lys Val Ser Ile
            260                 265                 270

Glu Gly Asp Thr Asn Glu Val Pro Lys Ala Glu Leu Glu Lys Leu Leu
        275                 280                 285

Thr Met Lys Pro Gly Lys Trp Tyr Glu Arg Gln Gln Met Thr Ala Val
290                 295                 300

Leu Gly Glu Ile Gln Asn Arg Met Gly Ser Ala Gly Tyr Ala Tyr Ser
305                 310                 315                 320
```

-continued

```
Glu Ile Ser Val Gln Pro Leu Pro Asn Ala Glu Thr Lys Thr Val Asp
            325                 330                 335
Phe Val Leu His Ile Glu Pro Gly Arg Lys Ile Tyr Val Asn Glu Ile
        340                 345                 350
His Ile Thr Gly Asn Asn Lys Thr Arg Asp Glu Val Val Arg Arg Glu
    355                 360                 365
Leu Arg Gln Met Glu Ser Ala Pro Tyr Asp Thr Ser Lys Leu Gln Arg
370                 375                 380
Ser Lys Glu Arg Val Glu Leu Leu Gly Tyr Phe Asp Asn Val Gln Phe
385                 390                 395                 400
Asp Ala Val Pro Leu Ala Gly Thr Pro Asp Lys Val Asp Leu Asn Met
                405                 410                 415
Ser Leu Thr Glu Arg Ser Thr Gly Ser Leu Asp Leu Ser Ala Gly Trp
            420                 425                 430
Val Gln Asp Thr Gly Leu Val Met Ser Ala Gly Val Ser Gln Asp Asn
        435                 440                 445
Leu Phe Gly Thr Gly Lys Ser Ala Ala Leu Arg Ala Ser Arg Ser Lys
    450                 455                 460
Thr Thr Leu Asn Gly Ser Leu Ser Phe Thr Asp Pro Tyr Phe Thr Ala
465                 470                 475                 480
Asp Gly Val Ser Leu Gly Tyr Asp Val Tyr Gly Lys Ala Phe Asp Pro
                485                 490                 495
Arg Lys Ala Ser Thr Ser Ile Lys Gln Tyr Lys Thr Thr Thr Ala Gly
            500                 505                 510
Ala Gly Ile Arg Met Ser Val Pro Val Thr Glu Tyr Asp Arg Val Asn
        515                 520                 525
Phe Gly Leu Val Ala Glu His Leu Thr Val Asn Thr Tyr Asn Lys Ala
    530                 535                 540
Pro Lys His Tyr Ala Asp Phe Ile Lys Lys Tyr Gly Lys Thr Asp Gly
545                 550                 555                 560
Thr Asp Gly Ser Phe Lys Gly Trp Leu Tyr Lys Gly Thr Val Gly Trp
                565                 570                 575
Gly Arg Asn Lys Thr Asp Ser Ala Leu Trp Pro Thr Arg Gly Tyr Leu
            580                 585                 590
Thr Gly Val Asn Ala Glu Ile Ala Leu Pro Gly Ser Lys Leu Gln Tyr
        595                 600                 605
Tyr Ser Ala Thr His Asn Gln Thr Trp Phe Phe Pro Leu Ser Lys Thr
    610                 615                 620
Phe Thr Leu Met Leu Gly Gly Glu Val Gly Ile Ala Gly Gly Tyr Gly
625                 630                 635                 640
Arg Thr Lys Glu Ile Pro Phe Phe Glu Asn Phe Tyr Gly Gly Gly Leu
                645                 650                 655
Gly Ser Val Arg Gly Tyr Glu Ser Gly Thr Leu Gly Pro Lys Val Tyr
            660                 665                 670
Asp Glu Tyr Gly Glu Lys Ile Ser Tyr Gly Gly Asn Lys Lys Ala Asn
        675                 680                 685
Val Ser Ala Glu Leu Leu Phe Pro Met Pro Gly Ala Lys Asp Ala Arg
    690                 695                 700
Thr Val Arg Leu Ser Leu Phe Ala Asp Ala Gly Ser Val Trp Asp Gly
705                 710                 715                 720
Lys Thr Tyr Asp Asp Asn Ser Ser Ala Thr Gly Gly Arg Val Gln
                725                 730                 735
Asn Ile Tyr Gly Ala Gly Asn Thr His Lys Ser Thr Phe Thr Asn Glu
```

```
                      740                 745                 750
Leu Arg Tyr Ser Ala Gly Gly Ala Val Thr Trp Leu Ser Pro Leu Gly
            755                 760                 765

Pro Met Lys Phe Ser Tyr Ala Tyr Pro Leu Lys Lys Pro Glu Asp
        770                 775                 780

Glu Ile Gln Arg Phe Gln Phe Gln Leu Gly Thr Thr Phe
785                 790                 795

<210> SEQ ID NO 15
<211> LENGTH: 6
<212> TYPE: PRT
<213> ORGANISM: Artificial Sequence
<220> FEATURE:
<223> OTHER INFORMATION: Linker

<400> SEQUENCE: 15

Gly Ser Gly Gly Gly Gly
1               5

<210> SEQ ID NO 16
<211> LENGTH: 8
<212> TYPE: PRT
<213> ORGANISM: Artificial Sequence
<220> FEATURE:
<223> OTHER INFORMATION: Linker

<400> SEQUENCE: 16

Gly Ser Gly Ser Gly Gly Gly Gly
1               5

<210> SEQ ID NO 17
<211> LENGTH: 6
<212> TYPE: PRT
<213> ORGANISM: Artificial Sequence
<220> FEATURE:
<223> OTHER INFORMATION: Histidine tag

<400> SEQUENCE: 17

His His His His His His
1               5

<210> SEQ ID NO 18
<211> LENGTH: 26
<212> TYPE: DNA
<213> ORGANISM: Artificial Sequence
<220> FEATURE:
<223> OTHER INFORMATION: Immunostimulatory oligodeoxynucleotide
<220> FEATURE:
<221> NAME/KEY: modified_base
<222> LOCATION: 1, 3, 5, 7, 9, 11, 13, 15, 17, 19, 21, 23, 25
<223> OTHER INFORMATION: 'n' is 'i' (Inosine)

<400> SEQUENCE: 18
ncncncncnc ncncncncnc ncncnc                                        26

<210> SEQ ID NO 19
<211> LENGTH: 11
<212> TYPE: PRT
<213> ORGANISM: Artificial Sequence
<220> FEATURE:
<223> OTHER INFORMATION: Polycationic oligopeptide

<400> SEQUENCE: 19

Lys Leu Lys Leu Leu Leu Leu Leu Lys Leu Lys
1               5                   10
```

<210> SEQ ID NO 20
<211> LENGTH: 274
<212> TYPE: PRT
<213> ORGANISM: Neisseria meningitidis

<400> SEQUENCE: 20

```
Met Asn Arg Thr Ala Phe Cys Cys Leu Ser Leu Thr Thr Ala Leu Ile
1               5                   10                  15
Leu Thr Ala Cys Ser Ser Gly Gly Gly Val Ala Ala Asp Ile Gly
            20                  25                  30
Ala Gly Leu Ala Asp Ala Leu Thr Ala Pro Leu Asp His Lys Asp Lys
        35                  40                  45
Gly Leu Gln Ser Leu Thr Leu Asp Gln Ser Val Arg Lys Asn Glu Lys
    50                  55                  60
Leu Lys Leu Ala Ala Gln Gly Ala Glu Lys Thr Tyr Gly Asn Gly Asp
65                  70                  75                  80
Ser Leu Asn Thr Gly Lys Leu Lys Asn Asp Lys Val Ser Arg Phe Asp
                85                  90                  95
Phe Ile Arg Gln Ile Glu Val Asp Gly Gln Leu Ile Thr Leu Glu Ser
            100                 105                 110
Gly Glu Phe Gln Val Tyr Lys Gln Ser His Ser Ala Leu Thr Ala Phe
        115                 120                 125
Gln Thr Glu Gln Ile Gln Asp Ser Glu His Ser Gly Lys Met Val Ala
    130                 135                 140
Lys Arg Gln Phe Arg Ile Gly Asp Ile Ala Gly Glu His Thr Ser Phe
145                 150                 155                 160
Asp Lys Leu Pro Glu Gly Gly Arg Ala Thr Tyr Arg Gly Thr Ala Phe
                165                 170                 175
Gly Ser Asp Asp Ala Gly Gly Lys Leu Thr Tyr Thr Ile Asp Phe Ala
            180                 185                 190
Ala Lys Gln Gly Asn Gly Lys Ile Glu His Leu Lys Ser Pro Glu Leu
        195                 200                 205
Asn Val Asp Leu Ala Ala Ala Asp Ile Lys Pro Asp Gly Lys Arg His
    210                 215                 220
Ala Val Ile Ser Gly Ser Val Leu Tyr Asn Gln Ala Glu Lys Gly Ser
225                 230                 235                 240
Tyr Ser Leu Gly Ile Phe Gly Gly Lys Ala Gln Glu Val Ala Gly Ser
                245                 250                 255
Ala Glu Val Lys Thr Val Asn Gly Ile Arg His Ile Gly Leu Ala Ala
            260                 265                 270
Lys Gln
```

<210> SEQ ID NO 21
<211> LENGTH: 273
<212> TYPE: PRT
<213> ORGANISM: Neisseria meningitidis

<400> SEQUENCE: 21

```
Met Asn Arg Thr Ala Phe Cys Cys Leu Ser Leu Thr Ala Ala Leu Ile
1               5                   10                  15
Leu Thr Ala Cys Ser Ser Gly Gly Gly Val Ala Ala Asp Ile Gly
            20                  25                  30
Ala Gly Leu Ala Asp Ala Leu Thr Ala Pro Leu Asp His Lys Asp Lys
        35                  40                  45
Ser Leu Gln Ser Leu Thr Leu Asp Gln Ser Val Arg Lys Asn Glu Lys
```

```
       50                  55                  60
Leu Lys Leu Ala Ala Gln Gly Ala Glu Lys Thr Tyr Gly Asn Gly Asp
 65                  70                  75                  80

Ser Leu Asn Thr Gly Lys Leu Lys Asn Asp Lys Val Ser Arg Phe Asp
                 85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
            115                 120                 125

Gln Ile Glu Lys Ile Asn Asn Pro Asp Lys Ile Asp Ser Leu Ile Asn
130                 135                 140

Gln Arg Ser Phe Leu Val Ser Gly Leu Gly Gly Glu His Thr Ala Phe
145                 150                 155                 160

Asn Gln Leu Pro Asp Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
            195                 200                 205

Val Glu Leu Ala Ala Ala Glu Leu Lys Ala Asp Glu Lys Ser His Ala
210                 215                 220

Val Ile Leu Gly Asp Thr Arg Tyr Gly Ser Glu Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Gly Glu Lys Val His Glu Ile Gly Ile Ala Gly Lys
            260                 265                 270

Gln

<210> SEQ ID NO 22
<211> LENGTH: 281
<212> TYPE: PRT
<213> ORGANISM: Neisseria meningitidis

<400> SEQUENCE: 22

Met Asn Arg Thr Ala Phe Cys Cys Leu Ser Leu Thr Thr Ala Leu Ile
 1               5                  10                  15

Leu Thr Ala Cys Ser Ser Gly Gly Gly Ser Gly Gly Gly Gly Gly Val
                20                  25                  30

Ala Ala Asp Ile Gly Thr Gly Leu Ala Asp Ala Leu Thr Ala Pro Leu
            35                  40                  45

Asp His Lys Asp Lys Gly Leu Lys Ser Leu Thr Leu Glu Asp Ser Ile
        50                  55                  60

Pro Gln Asn Gly Thr Leu Thr Leu Ser Ala Gln Gly Ala Glu Lys Thr
 65                  70                  75                  80

Phe Lys Ala Gly Asp Lys Asp Asn Ser Leu Asn Thr Gly Lys Leu Lys
                 85                  90                  95

Asn Asp Lys Ile Ser Arg Phe Asp Phe Val Gln Lys Ile Glu Val Asp
            100                 105                 110

Gly Gln Thr Ile Thr Leu Ala Ser Gly Glu Phe Gln Ile Tyr Lys Gln
            115                 120                 125

Asn His Ser Ala Val Val Ala Leu Gln Ile Glu Lys Ile Asn Asn Pro
130                 135                 140

Asp Lys Thr Asp Ser Leu Ile Asn Gln Arg Ser Phe Leu Val Ser Gly
```

```
                      145                 150                 155                 160
Leu Gly Gly Glu His Thr Ala Phe Asn Gln Leu Pro Gly Gly Lys Ala
                      165                 170                 175

Glu Tyr His Gly Lys Ala Phe Ser Ser Asp Pro Asn Gly Arg Leu
                180                 185                 190

His Tyr Ser Ile Asp Phe Thr Lys Gln Gly Tyr Gly Arg Ile Glu
                195                 200                 205

His Leu Lys Thr Leu Glu Gln Asn Val Glu Leu Ala Ala Ala Glu Leu
                210                 215                 220

Lys Ala Asp Glu Lys Ser His Ala Val Ile Leu Gly Asp Thr Arg Tyr
225                 230                 235                 240

Gly Ser Glu Glu Lys Gly Thr Tyr His Leu Ala Leu Phe Gly Asp Arg
                245                 250                 255

Ala Gln Glu Ile Ala Gly Ser Ala Thr Val Lys Ile Gly Glu Lys Val
                260                 265                 270

His Glu Ile Gly Ile Ala Gly Lys Gln
                275                 280

<210> SEQ ID NO 23
<211> LENGTH: 260
<212> TYPE: PRT
<213> ORGANISM: Neisseria meningitidis

<400> SEQUENCE: 23

Cys Ser Ser Gly Gly Gly Ser Gly Gly Gly Val Thr Ala Asp
1               5                   10                  15

Ile Gly Thr Gly Leu Ala Asp Ala Leu Thr Ala Pro Leu Asp His Lys
                20                  25                  30

Asp Lys Gly Leu Lys Ser Leu Thr Leu Glu Asp Ser Ile Ser Gln Asn
            35                  40                  45

Gly Thr Leu Thr Leu Ser Ala Gln Gly Ala Glu Lys Thr Tyr Gly Asn
        50                  55                  60

Gly Asp Ser Leu Asn Thr Gly Lys Leu Lys Asn Asp Lys Val Ser Arg
65                  70                  75                  80

Phe Asp Phe Ile Arg Gln Ile Glu Val Asp Gly Gln Leu Ile Thr Leu
                85                  90                  95

Glu Ser Gly Glu Phe Gln Val Tyr Lys Gln Ser His Ser Ala Leu Thr
            100                 105                 110

Ala Leu Gln Thr Glu Gln Glu Gln Asp Pro Glu His Ser Glu Lys Met
        115                 120                 125

Val Ala Lys Arg Arg Phe Arg Ile Gly Asp Ile Ala Gly Glu His Thr
    130                 135                 140

Ser Phe Asp Lys Leu Pro Lys Asp Val Met Ala Thr Tyr Arg Gly Thr
145                 150                 155                 160

Ala Phe Gly Ser Asp Asp Ala Gly Gly Lys Leu Thr Tyr Thr Ile Asp
                165                 170                 175

Phe Ala Ala Lys Gln Gly His Gly Lys Ile Glu His Leu Lys Ser Pro
            180                 185                 190

Glu Leu Asn Val Asp Leu Ala Val Ala Tyr Ile Lys Pro Asp Glu Lys
        195                 200                 205

His His Ala Val Ile Ser Gly Ser Val Leu Tyr Asn Gln Asp Glu Lys
    210                 215                 220

Gly Ser Tyr Ser Leu Gly Ile Phe Gly Glu Lys Ala Gln Glu Val Ala
225                 230                 235                 240
```

```
Gly Ser Ala Glu Val Glu Thr Ala Asn Gly Ile His His Ile Gly Leu
            245                 250                 255

Ala Ala Lys Gln
            260

<210> SEQ ID NO 24
<211> LENGTH: 262
<212> TYPE: PRT
<213> ORGANISM: Neisseria meningitidis

<400> SEQUENCE: 24

Cys Ser Ser Gly Gly Gly Ser Gly Gly Gly Gly Val Ala Ala Asp
1               5                   10                  15

Ile Gly Ala Gly Leu Ala Asp Ala Leu Thr Ala Pro Leu Asp His Lys
            20                  25                  30

Asp Lys Gly Leu Lys Ser Leu Thr Leu Glu Asp Ser Ile Ser Gln Asn
        35                  40                  45

Gly Thr Leu Thr Leu Ser Ala Gln Gly Ala Glu Arg Thr Phe Lys Ala
    50                  55                  60

Gly Asp Lys Asp Asn Ser Leu Asn Thr Gly Lys Leu Lys Asn Asp Lys
65                  70                  75                  80

Ile Ser Arg Phe Asp Phe Ile Arg Gln Ile Glu Val Asp Gly Gln Leu
                85                  90                  95

Ile Thr Leu Glu Ser Gly Glu Phe Gln Val Tyr Lys Gln Ser His Ser
            100                 105                 110

Ala Leu Thr Ala Leu Gln Thr Glu Gln Val Gln Asp Ser Glu His Ser
        115                 120                 125

Gly Lys Met Val Ala Lys Arg Gln Phe Arg Ile Gly Asp Ile Val Gly
    130                 135                 140

Glu His Thr Ser Phe Asp Lys Leu Pro Lys Asp Val Met Ala Thr Tyr
145                 150                 155                 160

Arg Gly Thr Ala Phe Gly Ser Asp Asp Ala Gly Gly Lys Leu Thr Tyr
                165                 170                 175

Thr Ile Asp Ala Ala Lys Gln Gly His Gly Lys Ile Glu His Leu Lys
            180                 185                 190

Ser Pro Glu Leu Asn Val Asp Leu Ala Ala Ala Asp Ile Lys Pro Asp
        195                 200                 205

Glu Lys His His Ala Val Ile Ser Gly Ser Val Leu Tyr Asn Gln Ala
    210                 215                 220

Glu Lys Gly Ser Tyr Ser Leu Gly Ile Phe Gly Gly Gln Ala Gln Glu
225                 230                 235                 240

Val Ala Gly Ser Ala Glu Val Glu Thr Ala Asn Gly Ile Arg His Ile
                245                 250                 255

Gly Leu Ala Ala Lys Gln
            260

<210> SEQ ID NO 25
<211> LENGTH: 261
<212> TYPE: PRT
<213> ORGANISM: Neisseria meningitidis

<400> SEQUENCE: 25

Cys Ser Ser Gly Ser Gly Ser Gly Gly Gly Val Ala Ala Asp Ile
1               5                   10                  15

Gly Thr Gly Leu Ala Asp Ala Leu Thr Ala Pro Leu Asp His Lys Asp
            20                  25                  30
```

```
Lys Gly Leu Lys Ser Leu Thr Leu Glu Asp Ser Ile Ser Gln Asn Gly
             35                  40                  45

Thr Leu Thr Leu Ser Ala Gln Gly Ala Glu Lys Thr Phe Lys Val Gly
         50                  55                  60

Asp Lys Asp Asn Ser Leu Asn Thr Gly Lys Leu Lys Asn Asp Lys Ile
 65                  70                  75                  80

Ser Arg Phe Asp Phe Val Gln Lys Ile Glu Val Asp Gly Gln Thr Ile
                 85                  90                  95

Thr Leu Ala Ser Gly Glu Phe Gln Ile Tyr Lys Gln Asp His Ser Ala
            100                 105                 110

Val Val Ala Leu Gln Ile Glu Lys Ile Asn Asn Pro Asp Lys Ile Asp
            115                 120                 125

Ser Leu Ile Asn Gln Arg Ser Phe Leu Val Ser Gly Leu Gly Gly Glu
130                 135                 140

His Thr Ala Phe Asn Gln Leu Pro Ser Gly Lys Ala Glu Tyr His Gly
145                 150                 155                 160

Lys Ala Phe Ser Ser Asp Asp Ala Gly Gly Lys Leu Thr Tyr Thr Ile
                165                 170                 175

Asp Phe Ala Ala Lys Gln Gly His Gly Lys Ile Glu His Leu Lys Thr
            180                 185                 190

Pro Glu Gln Asn Val Glu Leu Ala Ser Ala Glu Leu Lys Ala Asp Glu
            195                 200                 205

Lys Ser His Ala Val Ile Leu Gly Asp Thr Arg Tyr Gly Ser Glu Glu
            210                 215                 220

Lys Gly Thr Tyr His Leu Ala Leu Phe Gly Asp Arg Ala Gln Glu Ile
225                 230                 235                 240

Ala Gly Ser Ala Thr Val Lys Ile Arg Glu Lys Val His Glu Ile Gly
                245                 250                 255

Ile Ala Gly Lys Gln
            260

<210> SEQ ID NO 26
<211> LENGTH: 255
<212> TYPE: PRT
<213> ORGANISM: Neisseria meningitidis

<400> SEQUENCE: 26

Cys Ser Ser Gly Gly Gly Gly Val Ala Ala Asp Ile Gly Ala Gly Leu
 1               5                  10                  15

Ala Asp Ala Leu Thr Ala Pro Leu Asp His Lys Asp Lys Gly Leu Gln
             20                  25                  30

Ser Leu Thr Leu Asp Gln Ser Val Arg Lys Asn Glu Lys Leu Lys Leu
         35                  40                  45

Ala Ala Gln Gly Ala Glu Lys Thr Tyr Gly Asn Gly Asp Ser Leu Asn
     50                  55                  60

Thr Gly Lys Leu Lys Asn Asp Lys Val Ser Arg Phe Asp Phe Ile Arg
 65                  70                  75                  80

Gln Ile Glu Val Asp Gly Gln Leu Ile Thr Leu Glu Ser Gly Glu Phe
                 85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
            115                 120                 125

Phe Arg Ile Gly Asp Ile Ala Gly Glu His Thr Ser Phe Asp Lys Leu
130                 135                 140
```

-continued

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
            165                 170                 175

Gly Asn Gly Lys Ile Glu His Leu Lys Ser Pro Glu Leu Asn Val Asp
        180                 185                 190

Leu Ala Ala Ala Asp Ile Lys Pro Asp Gly Lys Arg His Ala Val Ile
    195                 200                 205

Ser Gly Ser Val Leu Tyr Asn Gln Ala Glu Lys Gly Ser Tyr Ser Leu
210                 215                 220

Gly Ile Phe Gly Lys Ala Gln Glu Val Ala Gly Ser Ala Glu Val
225                 230                 235                 240

Lys Thr Val Asn Gly Ile Arg His Ile Gly Leu Ala Ala Lys Gln
            245                 250                 255

<210> SEQ ID NO 27
<211> LENGTH: 6
<212> TYPE: PRT
<213> ORGANISM: Neisseria meningitidis

<400> SEQUENCE: 27

Asp Gln Ser Val Arg Lys
1               5

<210> SEQ ID NO 28
<211> LENGTH: 6
<212> TYPE: PRT
<213> ORGANISM: Neisseria meningitidis

<400> SEQUENCE: 28

Gln Ser Val Arg Lys Asn
1               5

<210> SEQ ID NO 29
<211> LENGTH: 6
<212> TYPE: PRT
<213> ORGANISM: Neisseria meningitidis

<400> SEQUENCE: 29

Ser Val Arg Lys Asn Glu
1               5

<210> SEQ ID NO 30
<211> LENGTH: 6
<212> TYPE: PRT
<213> ORGANISM: Neisseria meningitidis

<400> SEQUENCE: 30

Val Arg Lys Asn Glu Lys
1               5

<210> SEQ ID NO 31
<211> LENGTH: 6
<212> TYPE: PRT
<213> ORGANISM: Neisseria meningitidis

<400> SEQUENCE: 31

Arg Lys Asn Glu Lys Leu
1               5

<210> SEQ ID NO 32

```
<211> LENGTH: 6
<212> TYPE: PRT
<213> ORGANISM: Neisseria meningitidis

<400> SEQUENCE: 32

Lys Asn Glu Lys Leu Lys
1               5

<210> SEQ ID NO 33
<211> LENGTH: 6
<212> TYPE: PRT
<213> ORGANISM: Neisseria meningitidis

<400> SEQUENCE: 33

Asn Glu Lys Leu Lys Leu
1               5

<210> SEQ ID NO 34
<211> LENGTH: 6
<212> TYPE: PRT
<213> ORGANISM: Neisseria meningitidis

<400> SEQUENCE: 34

Glu Lys Leu Lys Leu Ala
1               5

<210> SEQ ID NO 35
<211> LENGTH: 6
<212> TYPE: PRT
<213> ORGANISM: Neisseria meningitidis

<400> SEQUENCE: 35

Pro Glu Gly Gly Arg Ala
1               5

<210> SEQ ID NO 36
<211> LENGTH: 6
<212> TYPE: PRT
<213> ORGANISM: Neisseria meningitidis

<400> SEQUENCE: 36

Lys Thr Val Asn Gly Ile
1               5

<210> SEQ ID NO 37
<211> LENGTH: 6
<212> TYPE: PRT
<213> ORGANISM: Neisseria meningitidis

<400> SEQUENCE: 37

Thr Val Asn Gly Ile Arg
1               5

<210> SEQ ID NO 38
<211> LENGTH: 6
<212> TYPE: PRT
<213> ORGANISM: Neisseria meningitidis

<400> SEQUENCE: 38

Glu Asp Ser Ile Ser Gln
1               5

<210> SEQ ID NO 39
<211> LENGTH: 6
<212> TYPE: PRT
```

<213> ORGANISM: Neisseria meningitidis

<400> SEQUENCE: 39

Asp Ser Ile Ser Gln Asn
1               5

<210> SEQ ID NO 40
<211> LENGTH: 6
<212> TYPE: PRT
<213> ORGANISM: Neisseria meningitidis

<400> SEQUENCE: 40

Ser Ile Ser Gln Asn Gly
1               5

<210> SEQ ID NO 41
<211> LENGTH: 6
<212> TYPE: PRT
<213> ORGANISM: Neisseria meningitidis

<400> SEQUENCE: 41

Ile Ser Gln Asn Gly Thr
1               5

<210> SEQ ID NO 42
<211> LENGTH: 6
<212> TYPE: PRT
<213> ORGANISM: Neisseria meningitidis

<400> SEQUENCE: 42

Ser Gln Asn Gly Thr Leu
1               5

<210> SEQ ID NO 43
<211> LENGTH: 6
<212> TYPE: PRT
<213> ORGANISM: Neisseria meningitidis

<400> SEQUENCE: 43

Gln Asn Gly Thr Leu Thr
1               5

<210> SEQ ID NO 44
<211> LENGTH: 6
<212> TYPE: PRT
<213> ORGANISM: Neisseria meningitidis

<400> SEQUENCE: 44

Asn Gly Thr Leu Thr Leu
1               5

<210> SEQ ID NO 45
<211> LENGTH: 6
<212> TYPE: PRT
<213> ORGANISM: Neisseria meningitidis

<400> SEQUENCE: 45

Gly Thr Leu Thr Leu Ser
1               5

<210> SEQ ID NO 46
<211> LENGTH: 6
<212> TYPE: PRT
<213> ORGANISM: Neisseria meningitidis

<400> SEQUENCE: 46

Pro Lys Asp Val Met Ala
1               5

<210> SEQ ID NO 47
<211> LENGTH: 6
<212> TYPE: PRT
<213> ORGANISM: Neisseria meningitidis

<400> SEQUENCE: 47

Glu Thr Ala Asn Gly Ile
1               5

<210> SEQ ID NO 48
<211> LENGTH: 6
<212> TYPE: PRT
<213> ORGANISM: Neisseria meningitidis

<400> SEQUENCE: 48

Thr Ala Asn Gly Ile His
1               5

<210> SEQ ID NO 49
<211> LENGTH: 327
<212> TYPE: PRT
<213> ORGANISM: Neisseria meningitidis

<400> SEQUENCE: 49

Ala Thr Asn Asp Asp Val Lys Lys Ala Ala Thr Val Ala Ile Ala
1               5                   10                  15

Ala Ala Tyr Asn Asn Gly Gln Glu Ile Asn Gly Phe Lys Ala Gly Glu
                20                  25                  30

Thr Ile Tyr Asp Ile Asp Glu Asp Gly Thr Ile Thr Lys Lys Asp Ala
            35                  40                  45

Thr Ala Ala Asp Val Glu Ala Asp Asp Phe Lys Gly Leu Gly Leu Lys
        50                  55                  60

Lys Val Val Thr Asn Leu Thr Lys Thr Val Asn Glu Asn Lys Gln Asn
65                  70                  75                  80

Val Asp Ala Lys Val Lys Ala Ala Glu Ser Glu Ile Glu Lys Leu Thr
                85                  90                  95

Thr Lys Leu Ala Asp Thr Asp Ala Ala Leu Ala Asp Thr Asp Ala Ala
            100                 105                 110

Leu Asp Ala Thr Thr Asn Ala Leu Asn Lys Leu Gly Glu Asn Ile Thr
        115                 120                 125

Thr Phe Ala Glu Glu Thr Lys Thr Asn Ile Val Lys Ile Asp Glu Lys
    130                 135                 140

Leu Glu Ala Val Ala Asp Thr Val Asp Lys His Ala Glu Ala Phe Asn
145                 150                 155                 160

Asp Ile Ala Asp Ser Leu Asp Glu Thr Asn Thr Lys Ala Asp Glu Ala
                165                 170                 175

Val Lys Thr Ala Asn Glu Ala Lys Gln Thr Ala Glu Glu Thr Lys Gln
            180                 185                 190

Asn Val Asp Ala Lys Val Lys Ala Ala Glu Thr Ala Ala Gly Lys Ala
        195                 200                 205

Glu Ala Ala Ala Gly Thr Ala Asn Thr Ala Ala Asp Lys Ala Glu Ala
    210                 215                 220

Val Ala Ala Lys Val Thr Asp Ile Lys Ala Asp Ile Ala Thr Asn Lys
225                 230                 235                 240

-continued

```
Asp Asn Ile Ala Lys Lys Ala Asn Ser Ala Asp Val Tyr Thr Arg Glu
            245                 250                 255

Glu Ser Asp Ser Lys Phe Val Arg Ile Asp Gly Leu Asn Ala Thr Thr
            260                 265                 270

Glu Lys Leu Asp Thr Arg Leu Ala Ser Ala Glu Lys Ser Ile Ala Asp
            275                 280                 285

His Asp Thr Arg Leu Asn Gly Leu Asp Lys Thr Val Ser Asp Leu Arg
            290                 295                 300

Lys Glu Thr Arg Gln Gly Leu Ala Glu Gln Ala Ala Leu Ser Gly Leu
305                 310                 315                 320

Phe Gln Pro Tyr Asn Val Gly
                325
```